US012186157B2

(12) United States Patent
Hansen et al.

(10) Patent No.: US 12,186,157 B2
(45) Date of Patent: *Jan. 7, 2025

(54) WOUND DRESSING WITH ELECTRODE MULTIPLEXING AND RELATED METHODS

(71) Applicant: Coloplast A/S, Humlebaek (DK)

(72) Inventors: Jais Ask Hansen, Jaegerspris (DK); Lars Erup Larsen, Stenloese (DK); Niels Hvid, Vedbaek (DK); Finn Speiermann, Virum (DK)

(73) Assignee: Coloplast A/S, Humlebaek (DK)

( * ) Notice: Subject to any disclaimer, the term of this patent is extended or adjusted under 35 U.S.C. 154(b) by 980 days.

This patent is subject to a terminal disclaimer.

(21) Appl. No.: 17/058,684

(22) PCT Filed: Jan. 31, 2019

(86) PCT No.: PCT/DK2019/050039
§ 371 (c)(1),
(2) Date: Nov. 25, 2020

(87) PCT Pub. No.: WO2019/238183
PCT Pub. Date: Dec. 19, 2019

(65) Prior Publication Data
US 2021/0205141 A1    Jul. 8, 2021

(30) Foreign Application Priority Data

Jun. 15, 2018 (DK) ............................. PA 2018 70403
Dec. 20, 2018 (WO) ................. PCT/DK2018/050384

(51) Int. Cl.
  *A61F 13/00* (2024.01)
  *A61F 13/42* (2006.01)
  *A61F 13/84* (2006.01)

(52) U.S. Cl.
  CPC ........ *A61F 13/00055* (2013.01); *A61F 13/42* (2013.01); *A61F 2013/00089* (2013.01); *A61F 2013/424* (2013.01); *A61F 2013/8482* (2013.01)

(58) Field of Classification Search
  CPC .... A61F 13/42; A61F 13/84; A61F 13/00055; A61F 13/00655; A61F 2013/00089;
  (Continued)

(56) References Cited

U.S. PATENT DOCUMENTS 6,171,289 B1   1/2001   Millot et al.
11,872,108 B2 *  1/2024   Hansen ..................... A61F 5/44
  (Continued)

FOREIGN PATENT DOCUMENTS

DE    19953062 A1   5/2000
GB     2542093 A    3/2017
  (Continued)

OTHER PUBLICATIONS

Raj, Aswinth, Multiplexer Circuit and How it Works, Jul. 6, 2018, Circuit Digest, [retreived on Aug. 9, 2023]. Retreived from the internet <U LR: https://circuitdigest.com/tutorial/what-is-multiplexer-circuit-and-how-it-works> (Year: 2018).

*Primary Examiner* — Keri J Nelson
*Assistant Examiner* — Daniel A Miller
(74) *Attorney, Agent, or Firm* — Coloplast Corp., Coloplast A/S; Nick Baumann

(57) ABSTRACT

A wound dressing is disclosed. A wound dressing comprises a first adhesive layer, an electrode assembly, a monitor interface and a multiplexer. The first adhesive layer comprises a proximal surface configured for attachment of the wound dressing to a skin surface of a user. The electrode assembly comprises a plurality of electrodes including a first set of first electrodes. The monitor interface is configured to form a mechanical and electrical connection with a monitor device. The monitor interface comprises a coupling part and a plurality of terminals including a first terminal. The multiplexer comprises a number of N input pins and a number of M output pins. The N input pins include a first set of first input pins for connection to first electrodes of the first set of first electrodes, the first set of first pins including a first primary input pin and a first secondary input pin, and the M output pins include a first output pin. The first primary input pin is connected to a first primary electrode of the first set of (Continued)

first electrodes and the first secondary input pin is connected to a first secondary electrode of the first set of first electrodes, and the first output pin is connected to the first terminal of the monitor interface. The multiplexer is configured to connect the first primary input pin to the first output pin in a first multiplexer configuration and to connect the first secondary input pin to the first output pin in a second multiplexer configuration.

20 Claims, 16 Drawing Sheets

(58) Field of Classification Search
CPC ........ A61F 2013/424; A61F 2013/8482; A61F 2013/00961; A61F 5/4404; A61F 5/443; A61B 5/251; A61B 5/282; A61B 5/257

USPC .......................................................... 602/42
See application file for complete search history.

(56) References Cited

U.S. PATENT DOCUMENTS

| 2008/0004536 A1 | 1/2008 | Baxi et al. |
| 2010/0036230 A1 | 2/2010 | Greene et al. |
| 2016/0081580 A1* | 3/2016 | Bergelin ................ A61B 5/445 600/554 |
| 2020/0289346 A1* | 9/2020 | Hansen ................... A61B 5/257 |

FOREIGN PATENT DOCUMENTS

| KR | 20120003987 A | 1/2012 |
| WO | 2007098762 A1 | 9/2007 |

* cited by examiner

WOUND DRESSING WITH ELECTRODE MULTIPLEXING AND RELATED METHODS

The present disclosure relates to wound dressings and in particular to wound dressings with sensing and multiplexing capabilities to facilitate monitoring of the wound/wound dressing during use of the wound dressing.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
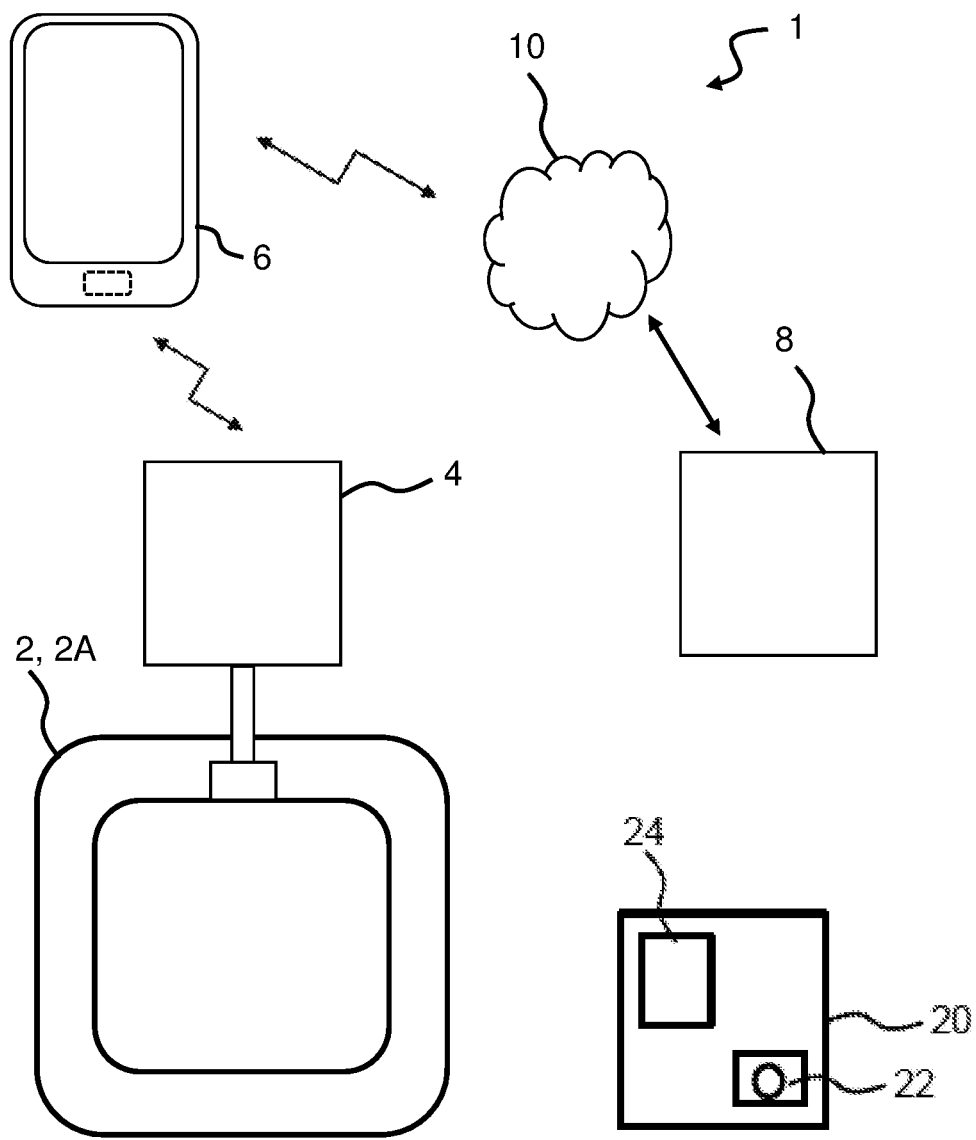
FIG. 1 illustrates an exemplary wound dressing system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

In the following, whenever referring to proximal side or surface of a layer, an element, a device or part of a device, the referral is to the skin-facing side or surface when a user wears the wound dressing. Likewise, whenever referring to the distal side or surface of a layer, an element, a device or part of a device, the referral is to the side or surface facing away from the skin when a user wears the wound dressing. In other words, the proximal side or surface is the side or surface closest to the user when the wound dressing is fitted on a user and the distal side is the opposite side or surface— the side or surface furthest away from the user in use.

The axial direction is defined as the direction away from the skin surface of the user when a user wears the wound dressing. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the wound dressing than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to a wound dressing system and devices thereof, such as a wound dressing, a monitor device, and optionally one or more accessory devices. Further, methods related to the wound dressing system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The wound dressing system may comprise a server device. The server device may be operated and/or controlled by the wound dressing system manufacturer and/or a service centre.

A wound dressing system comprising a wound dressing and/or a monitor device is disclosed, wherein the monitor device is a monitor device as described herein.

The present disclosure provides a wound dressing system and devices thereof, such as a wound dressing, a monitor device, and optionally one or more accessory devices which either alone or together facilitate reliable monitoring of the wound dressing and operating state thereof. Accordingly, the wound dressing system and devices thereof enable providing information to the user about the operating state of the wound dressing, and in turn optionally enable providing an indication to the user or a caretaker of the remaining time frame for replacing the wound dressing without experiencing leakage and/or to provide optimum wound healing conditions.

A wound dressing is disclosed, the wound dressing comprising a first adhesive layer with a proximal surface configured for attachment of the wound dressing to the skin surface of a user; an absorbent core layer; an electrode assembly comprising a plurality of electrodes optionally arranged on a distal side of the absorbent core layer; and a top layer on a distal side of the electrode assembly.

It is an advantage of the present disclosure that an optimum or improved use of a wound dressing is enabled and facilitated. In particular, the present disclosure facilitates that a wound dressing is not changed too early (leading to increased costs and/or material waste) nor too late (leading to adhesive failure, leakage and/or unsatisfactory wound healing conditions). Accordingly, the user or a health care professional is able to monitor and plan the use of the wound dressing.

Further, determination of moisture or wetting pattern types and classification of operating states of the wound dressing is useful in helping to reduce the risk of a user experiencing leakage from a wound dressing and/or in helping reduce the risk of unsatisfactory wound healing conditions. The present disclosure provides a simple, efficient, and easy-to-use wound dressing system with a high degree of comfort for a user.

In addition, it is an advantage of the present disclosure that the wound dressing with multiplexer capabilities disclosed herein facilitates a wound dressing with many electrodes, e.g. nine or more, while keeping the number of monitor terminals to a reasonable number, e.g. eight or less, such as four, five, six or seven.

The wound dressing comprises a first adhesive layer having a proximal surface configured for attachment of the wound dressing to the skin surface of a user. The first adhesive layer may comprise or be made of a first composition. The first composition may comprise silicone. The first adhesive layer may comprise a support layer with an adhesive material made of a first composition molded onto or otherwise attached to the support layer. The first composition may be a thermoset, curable adhesive material. An example of such adhesive material may be a silicone based adhesive material. The first composition may be a two-component system. Preferably, the first composition contains no solvent. Preferred first compositions include polyurethane, acrylic, silicone or polyethylene or polypropylene oxide based cross-linking types, e.g. as described in WO 2005/032401. The first composition may be a hotmelt type, which initially is heated to flow and subsequently cooled to gel or crosslink. Instead of curing upon cooling, the first composition may in some embodiments cure upon application of thermal energy.

The support layer of the first adhesive layer may be any suitable layer being water impermeable but vapour permeable. A suitable support layer may be a polyurethane film.

The first adhesive layer may have perforations or through-going openings arranged within an absorbing region, e.g. for allowing exudate from the wound to pass or flow through the perforations of the first adhesive layer to be absorbed by absorbent core layer arranged on the distal side of the first adhesive layer.

The perforations of the first adhesive layer may be made by punching, cutting or by applying high frequency mechanical vibrations, for example as disclosed in WO 2010/061228. The perforations may be arranged in a regular or random array, typically separated by 0.5 mm to 10 mm. The number of holes per $cm^2$ may be between 1 and 100, such as between 1 and 50 or even between 2 and 20.

The perforations of the first adhesive layer may have a diameter in the range from 0.5 mm to 10 mm, such as in the range from 1 mm to 8 mm. In one or more exemplary wound dressings, the perforations of the first adhesive layer have a diameter in the range from 1 mm to 5 mm, e.g. from 1.5 mm to 5 mm, and even in the range from 2 mm to 4 mm.

The wound dressing comprises an absorbent core layer also denoted an absorbent pad. The absorbent core layer may be a uniform material, or it may be a composite, for example in the form of a layered construction comprising layers of different texture and properties. The absorbent core layer may comprise foam, cellulose, super absorbent particles and/or fibres. The absorbent core layer may comprise a layer of foam facing the wound.

The absorbent core layer may comprise a polyurethane foam. The absorbent core layer may comprise a super absorbing layer.

The absorbent core layer and/or the first adhesive layer may contain active ingredients, such as ibuprofen, paracetamol, silver compounds or other medically active ingredients configured to reduce pain and/or to improve the healing of a wound. In one or more exemplary wound dressings, the absorbent core layer comprises a silver compound with antimicrobial properties.

The wound dressing comprises a top layer also denoted a backing layer. The top layer may be any suitable layer being water impermeable but vapour permeable. A suitable top layer may be a polyurethane film. The top layer is a protective layer protecting the absorbent core layer and other parts of the wound dressing from external strains and stress when the user wears the wound dressing. The electrodes, e.g. some or all the electrodes, may be arranged between the first adhesive layer and the top layer. The top layer may have a thickness in the range from 0.01 mm to 1.0 mm, e.g. in the range from 0.02 mm to 0.2 mm, such as 0.04 mm.

The wound dressing may comprise a release liner, such as a one-piece, two-piece or a three-piece release liner. The release liner is a protective layer that protects adhesive layer(s) during transport and storage and is peeled off by the user prior to applying the wound dressing on the skin.

The electrode assembly comprises a plurality of sensor points or sensor zones distributed along a distal surface or distal side of the absorbent core layer.

The plurality of electrodes optionally comprises a first set of first electrodes and optionally a second set of second electrodes, wherein a sensing part of a first electrode and a sensing part of the second electrode may form a sensor point. The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

A set of electrodes, such as the first set of electrodes and/or the second set of electrodes, may comprise one or a plurality of electrodes. In one or more exemplary electrode assemblies, a set of electrodes, such as the first set of electrodes and/or the second set of electrodes, may comprise one, two, three, four, five, or more electrodes. In one or more exemplary electrode assemblies, a first electrode of the first set of first electrodes forms a part of a first sensor point and a second sensor point of the plurality of sensor points. In one or more exemplary electrode assemblies, a first electrode of the first set of first electrodes forms a part of at least two sensor points, such as at least three sensor points. In one or more exemplary electrode assemblies, each of at least two first electrodes of the first set of first electrodes forms a part of at least two sensor points, such as at least three sensor points.

The first set of first electrodes may comprise one, two, three, or more electrodes. In one or more exemplary electrode assemblies, the first set of first electrodes comprises at least three electrodes, such as at least five electrodes.

In one or more exemplary electrode assemblies, a second electrode of the second set of second electrodes forms a part of a first sensor point and a third sensor point of the plurality of sensor points. In one or more exemplary electrode assemblies, a second electrode of the second set of second electrodes forms a part of at least two sensor points, such as at least three sensor points. In one or more exemplary electrode assemblies, each of at least two second electrodes of the second set of second electrodes forms a part of at least two sensor points, such as at least three sensor points.

The second set of second electrodes may comprise one, two, three, or more electrodes. In one or more exemplary electrode assemblies, the second set of second electrodes comprises at least three second electrodes, such as at least five electrodes.

A first set of first electrodes with N1 first electrodes $E\_1\_1, E\_1\_2, \ldots, E\_1\_N1$ and a second set of second electrodes with N2 second electrodes $E\_2\_1, E\_2\_2, \ldots, E\_2\_N2$ allow for an electrode assembly with N1 times N2 sensor points. In one or more exemplary wound dressings, the number N1 of first electrodes in the first set of first electrodes is in the range from 1 to 30, such as in the range from 3 to 25, or in the range from 4 to 20. The number N1 of first electrodes in the first set of first electrodes may be larger than 4, such as larger than 5 or even larger than 6. In one or more exemplary wound dressings, the number N2 of second electrodes in the second set of second electrodes is in the range from 1 to 30, such as in the range from 3 to 25, or in the range from 4 to 20. The number N2 of second electrodes in the second set of second electrodes may be larger than 4, such as larger than 5 or even larger than 6.

The electrode assembly comprises a plurality of sensor points optionally distributed along a distal surface of the absorbent core layer. In one or more exemplary electrode assemblies, the plurality of sensor points comprises at least nine sensor points. The plurality of sensor points may be arranged in a matrix configuration. The plurality of sensor points may comprise at least 20 sensor points. Two electrodes of the electrode assembly may form a sensor point. A first electrode $E\_1\_1$ and a second electrode $E\_2\_1$ may form a (first) sensor point $SP\_1\_1$ (first electrode pair). The first electrode $E\_1\_1$ and a second electrode $E\_2\_2$ may form a (second) sensor point $SP\_1\_2$ (second electrode pair). The first electrode $E\_1\_1$ and a second electrode $E\_2\_3$ may form a (third) sensor point $SP\_1\_3$ (third electrode pair). A first electrode $E\_1\_2$ and the second electrode $E\_2\_1$ may form a (fourth) sensor point $SP\_2\_1$ (fourth electrode pair). The first electrode $E\_1\_2$ and the second electrode $E\_2\_2$ may form a (fifth) sensor point $SP\_2\_2$ (fifth electrode pair). The first electrode $E\_1\_2$ and the second electrode $E\_2\_3$ may form a (sixth) sensor point $SP\_2\_3$ (sixth electrode pair). A first electrode $E\_1\_3$ and the second electrode $E\_2\_1$ may form a (seventh) sensor point $SP\_3\_1$ (seventh electrode pair). The first electrode $E\_1\_3$ and the second electrode $E\_2\_2$ may form a (eighth) sensor point $SP\_3\_2$ (eighth electrode pair). The first electrode $E\_1\_3$ and the second electrode $E\_2\_3$ may form a (ninth) sensor point $SP\_3\_3$ (ninth electrode pair).

A distance, such as a center-to-center distance, between two neighbouring sensor points may be in the range from 2 mm to 50 mm, such as about 30 mm. In one or more exemplary electrode assemblies, a distance, such as a center-to-center distance, between two neighbouring sensor points is in the range from 3 mm to 20 mm, such as in the range from 4 mm to 15 mm, e.g. about 5 mm, 6 mm, 7 mm, 8 mm, 9 mm, or 10 mm.

The electrode assembly may comprise one or more support layers including a first support layer. The first support layer may have a plurality of sensor point openings, e.g. for allowing exudate to pass through the first support layer. A sensor point opening of the first support layer may form a part of one or more sensor points of the electrode assembly.

The first set of electrodes may be printed or arranged on the first support layer. In one or more exemplary electrode assemblies, the first set of electrodes are printed on a proximal surface of the first support layer. The first set of electrodes may be printed on a distal surface of the first support layer.

The second set of electrodes may be printed or arranged on the first support layer. In one or more exemplary electrode assemblies, the second set of electrodes are printed on a proximal surface of the first support layer. The second set of electrodes may be printed on a distal surface of the first support layer. The second set of electrodes may be printed or arranged on a support layer surface different than the support layer surface on which the first set of electrodes is printed or arranged. Arranging the first set of electrodes and the second set of electrodes on different support layer surfaces allows for provision of a larger number of sensor points using a smaller number of electrodes.

The electrode assembly may comprise a second support layer. The second set of electrodes may be printed or arranged on the second support layer. In one or more exemplary electrode assemblies, the second set of electrodes are printed on a proximal surface of the second support layer. The second set of electrodes may be printed on a distal surface of the second support layer.

The second support layer may have a plurality of sensor point openings, e.g. for allowing exudate to pass through the second support layer. A sensor point opening of the second support layer may form a part of one or more sensor points of the electrode assembly.

A support layer, such as the first support layer and/or the second support layer, may comprise polymeric (e.g. polyurethane, PTFE, PVDF) and/or ceramic (e.g. alumina, silica) materials. In one or more exemplary wound dressings, the first support layer and/or the second support layer is/are made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the first support layer and/or the second support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly may comprise a spacing layer between the first support layer and the second support layer. A spacing layer between the first support layer and the second support layer may reduce the risk of false positives when detecting and/or determining moisture/liquid patterns or distributions. The spacing layer may have a plurality of sensor point openings, e.g. for allowing exudate to pass through the spacing layer. The spacing layer may be made of an absorbent material. The spacing layer may have a thickness in the range from 1 µm to 1 mm.

The electrode assembly/wound dressing may comprise one or more masking layers including a first masking layer isolating electrode parts of the plurality of electrodes. The first masking layer may isolate electrode parts of first electrodes of the first set of first electrodes. A masking layer may be made of a masking layer material, such as The first masking layer may be printed on the first support layer and optionally cover one or more parts of electrodes printed or arranged on the first support layer. In one or more exemplary electrode assemblies, the first masking layer is printed on the proximal side of the first support layer and covering one or more parts of first electrodes and/or second electrodes. In one or more exemplary electrode assemblies, the first masking layer is printed on the distal side of the first support layer and covering one or more parts of first electrodes and/or second electrodes.

The first masking layer may be printed on the second support layer and optionally cover one or more parts of electrodes printed or arranged on the second support layer. In one or more exemplary electrode assemblies, the first masking layer is printed on the proximal side of the second support layer and covering one or more parts of second electrodes. In one or more exemplary electrode assemblies, the first masking layer is printed on the distal side of the second support layer and covering one or more parts of second electrodes.

The first masking layer may be divided in a plurality of first masking layer parts. The first masking layer may be arranged between the absorbent core layer and at least parts of the first electrodes to electrically isolate the parts of the first electrodes from the absorbent core layer. The first masking layer may be arranged between the absorbent core layer and at least parts of the second electrodes to electrically isolate the parts of the second electrodes from the absorbent core layer.

The first masking layer may comprise one or more, such as a plurality of, sensor point openings. A sensor point opening of the first masking layer optionally overlaps at least one electrode of the electrode assembly when seen in the axial direction, e.g. to form a sensor point. For example, a sensor point opening of the first masking layer may overlap a (sensing) part of a first electrode of the first set of electrodes and a (sensing) part of a second electrode of the second set of electrodes.

The electrode assembly may comprise a second masking layer isolating electrode parts of the plurality of electrodes.

The second masking layer may be printed on the first support layer and optionally cover one or more parts of electrodes printed or arranged on the first support layer. In one or more exemplary electrode assemblies, the second masking layer is printed on the distal side of the first support layer and covering one or more parts of second electrodes.

The second masking layer may be printed on the second support layer and optionally cover one or more parts of electrodes printed or arranged on the second support layer. In one or more exemplary electrode assemblies, the second masking layer is printed or arranged on the proximal side of the second support layer and covering one or more parts of second electrodes. In one or more exemplary electrode assemblies, the second masking layer is printed or arranged on the distal side of the second support layer and covering one or more parts of second electrodes.

The second masking layer may be divided in a plurality of second masking layer parts. The second masking layer may be arranged between the absorbent core layer and at least parts of the second electrodes to electrically isolate the parts of the second electrodes from the absorbent core layer. The second masking layer may be arranged between the first support layer and at least parts of the second electrodes to electrically isolate the parts of the second electrodes from the first support layer. The second masking layer may be arranged between the spacing layer and at least parts of the second electrodes to electrically isolate the parts of the second electrodes from the spacing layer.

The second masking layer may comprise one or more, such as a plurality of, sensor point openings. A sensor point opening of the second masking layer optionally overlaps at least one electrode of the electrode assembly when seen in the axial direction, e.g. to form a sensor point. For example, a sensor point opening of the second masking layer may overlap a (sensing) part of a first electrode of the first set of electrodes and/or a (sensing) part of a second electrode of the second set of electrodes.

A masking layer, e.g. the first masking layer and/or the second masking layer, may comprise one or more, such as a plurality of, terminal openings. A terminal opening may overlap with one or more connection parts of electrodes. In one or more exemplary wound dressings, each terminal opening overlaps with a single connection part of an electrode. A masking layer, e.g. the first masking layer and/or the second masking layer, may comprise polymeric (e.g. polyurethane, PTFE, PVDF) and/or ceramic (e.g. alumina, silica) materials. In one or more exemplary wound dressings, the first masking layer and/or the second masking layer is/are made of or comprises thermoplastic polyurethane (TPU). In one or more exemplary wound dressings, the first masking layer and/or the second masking layer is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the first masking layer and/or the second masking layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The wound dressing comprises a monitor interface. The monitor interface may be configured for electrically and/or mechanically connecting the wound dressing (electrode assembly) to the monitor device. The monitor interface may be configured for wirelessly connecting the wound dressing to the monitor device. Thus, the monitor interface of the wound dressing is configured to electrically and/or mechanically couple the wound dressing and the monitor device.

The monitor interface of the wound dressing may comprise, e.g. as part of a first connector of the monitor interface, a coupling part for forming a mechanical connection, such as a releasable coupling between the monitor device and the wound dressing. The coupling part may be configured to engage with a coupling part of the monitor device for releasably coupling the monitor device to the wound dressing wound dressing.

The monitor interface of the wound dressing may comprise, e.g. as part of a first connector of the monitor interface, a plurality of terminals, such as two, three, four, five, six, seven, eight or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes (connection parts) of the wound dressing/electrode assembly. In one or more exemplary wound dressings, a first intermediate element may be arranged between the terminal elements and the first adhesive layer. The first intermediate element may cover or overlap terminal element(s) of the wound dressing when seen in the axial direction. Thus, the first adhesive layer may be protected or experience more evenly distributed mechanical stress from the terminal elements of the wound dressing, in turn reducing the risk of terminal elements penetrating or otherwise damaging the first adhesive layer. The first intermediate element may protect or mechanically and/or electrically shield the first adhesive layer from the terminal elements of the wound dressing.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part (with a distal end), a centre part, and/or a proximal part (with a proximal end). The centre part may be between the distal part and the proximal part. The proximal end/proximal part of a terminal element may contact a connection part of an electrode. A terminal element, such as the ground terminal element, the first terminal element, the second terminal element, the third terminal element, the fourth terminal element, the fifth terminal element and/or the sixth terminal element, may be gold plated copper.

In one or more exemplary wound dressings, connection parts of electrodes of the electrode assembly form respective terminals of the monitor interface.

The wound dressing may comprise a multiplexer. The multiplexer may comprise a number of N input pins and a number of M output pins. The number N of input pins may be larger than the number M of output pins, i.e. N>M. For example, the multiplexer may comprise at least nine input pins and one or two output pins. As another example, the multiplexer may comprise at least sixteen input pins and one or two output pins.

The N input pins may include a first set of first input pins for connection to first electrodes of the first set of first electrodes, the first set of first pins including a first primary input pin and a first secondary input pin, and the M output pins include a first output pin. The first primary input pin may be connected to a first primary electrode of the first set of first electrodes and the first secondary input pin may be connected to a first secondary electrode of the first set of first electrodes, and the first output pin may be connected to the first terminal of the monitor interface. The multiplexer may be configured to connect the first primary input pin to the first output pin in a first multiplexer configuration and to connect the first secondary input pin to the first output pin in a second multiplexer configuration. A wound dressing with said multiplexer facilitates a wound dressing with many electrodes, e.g. ten or more, while keeping the number of monitor terminals to a reasonable number, e.g. eight or less, such as four, five, six or seven.

The monitor interface may comprise a second terminal, wherein the M output pins may include a second output pin connected to the second terminal.

The plurality of electrodes may comprise a second set of second electrodes including a second primary electrode and a second secondary electrode. The N input pins may comprise a second set of second input pins for connection to second electrodes of the second set of second electrodes. A second primary input pin of the second set of second input pins may be connected to the second primary electrode and a second secondary input pin of the second set of second input pins may be connected to the second secondary electrode. The multiplexer may be configured to connect the second primary input pin to the second output pin in the first multiplexer configuration and to connect the second secondary input pin to the second output pin in the second multiplexer configuration.

The first set of first electrodes may comprise a first tertiary electrode. And, a first tertiary input pin of the first set of first input pins may be connected to the first tertiary input pin. The multiplexer may be configured to connect the first tertiary input pin to the first output pin in a third multiplexer configuration.

The second set of second electrodes may comprise a second tertiary electrode. A second tertiary input pin of the second set of second input pins may be connected to the second tertiary input pin. The multiplexer may be configured to connect the second tertiary input pin to the second output pin in a third multiplexer configuration.

The multiplexer may comprise a first control pin. The multiplexer may be configured to select a multiplexer configuration based on a first control signal received by the first control pin.

The multiplexer may comprise a second control pin. The multiplexer may be configured to select a multiplexer scheme based on a second control signal received by the second control pin.

The multiplexer may be embedded in the electrode assembly. Alternatively, the multiplexer may be embedded in the coupling part of the monitor interface.

A method of manufacturing a wound dressing is also disclosed. The method may comprise providing a first adhesive layer having a proximal surface configured for attachment of the wound dressing to a skin surface of a user. The method may further comprise arranging an absorbent core layer on a distal side of the first adhesive layer. The method may further comprise arranging an electrode assembly on the distal side of the absorbent core layer. The electrode assembly may comprise a plurality of electrodes and a multiplexer. The plurality of electrodes may comprise a first set of first electrodes, wherein a first primary electrode of the first set of first electrodes may be connected to a first primary input pin of the multiplexer and a first secondary electrode of the first set of first electrodes being may be connected to a first secondary input pin of the multiplexer. The method may further comprise arranging a monitor interface on the distal side of the absorbent core layer. The monitor interface may comprise a coupling part and a plurality of terminals including a first terminal for forming mechanical and electrical connection with a monitor device, such that a first output pin of the multiplexer is connected to the first terminal. Manufacturing a wound dressing having the above stated multiplexer will enable a wound dressing with many electrodes, e.g. ten or more, to connect with a monitor device having fewer monitor terminals, e.g. eight or less, such as four, five, six or seven.

A method of monitoring a wound dressing is also disclosed. The wound dressing may comprise a first adhesive layer, plurality of electrodes on a distal side of the first adhesive layer, a multiplexer, and a monitor interface. A first output pin of the multiplexer may be connected to a first terminal of the monitor interface and the plurality of electrodes may include a first set of first electrodes. The method may comprise selecting a first multiplexer configuration of the multiplexer. A first primary electrode of the first set of first electrodes may be connected to the first output pin in the first multiplexer configuration. The method may further comprise obtaining a first sensor signal from the first terminal of the monitor device. The method may further comprise selecting a second multiplexer configuration of the multiplexer. A first secondary electrode of the first set of first electrodes may be connected to the first output pin in the second multiplexer configuration. The method may further comprise obtaining a second sensor signal from the first terminal of the monitor device. Similar to above, this method allows sensor signals from many electrodes of the wound dressing to be monitored by a reasonable number of monitor terminals.

The monitor device comprises a processor and one or more interfaces, such as a first interface and/or a second interface. The monitor device may comprise a memory for storing wound data and/or parameter data based on the wound data.

The first interface is connected to the processor and the memory. The first interface is configured for collecting wound data from the wound dressing coupled to the first interface. The wound data, also denoted WD, comprises wound data from sensor points of the wound dressing, e.g. first wound data WD_1 from a first sensor point, e.g. a first electrode pair, of the wound dressing, second wound data WD_2 from a second sensor point, e.g. a second electrode pair, of the wound dressing, and optionally third wound data WD_3 from a third sensor point, e.g. a third electrode pair, of the wound dressing. In one or more exemplary monitor devices, the wound data comprises wound data for each sensor point of the wound dressing. For example, for a wound dressing with N sensor points, the wound data WD may comprise WD_1, WD_2, . . . , WD_N. The number N of sensor points of the wound dressing may be at least 9, such as at least 20 or even larger than 50.

The processor is configured to apply a processing scheme. To apply a processing scheme comprises to obtain parameter data based on the wound data, e.g. the first wound data WD_1, the second wound data WD_2, and the third wound data WD_3; and to determine an operating state of the wound dressing based on the parameter data. The parameter data may comprise one or more of first parameter data, also denoted P_1, based on the first wound data WD_1, second parameter data, also denoted P_2, based on the second wound data WD_2, and third parameter data, also denoted P_3, based on the third wound data WD_3.

The operating state of the wound dressing is optionally indicative of a degree of wetting of the absorbent core layer of the wound dressing. The operating state is optionally indicative of a degree of wetting of the distal surface of the absorbent core layer. The operating state may be indicative of a wetting pattern or wetting distribution on the distal surface or distal side of the absorbent core layer.

The monitor device is optionally configured to, in accordance with a determination that the operating state is a first operating state, transmit a first monitor signal comprising monitor data indicative of the first operating state of the wound dressing via the second interface. The first operating state of the wound dressing may correspond to a situation wherein the absorbent core layer is wetted to a first degree on the distal surface of the absorbent core layer and/or wherein a first wetting pattern is detected on the distal surface of the absorbent core layer.

The monitor device is optionally configured to, in accordance with a determination that the operating state is a second operating state, transmit a second monitor signal comprising monitor data indicative of the second operating state of the wound dressing via the second interface. The second operating state of the wound dressing may correspond to a situation wherein the absorbent core layer is wetted to a second degree (different from the first degree) on the distal surface of the absorbent core layer and/or wherein a second wetting pattern is detected on the distal surface of the absorbent core layer.

In one or more exemplary monitor devices, to determine an operating state of the wound dressing is based on a first criteria set based on first parameter data and/or second parameter data of the parameter data, wherein the operating state is determined to be the first operating state if the first criteria set is satisfied. The first criteria set optionally comprises a first primary criterion based on the first parameter data, and a first secondary criterion based on the second parameter data.

In one or more exemplary monitor devices, to determine an operating state of the wound dressing is based on a first threshold set comprising one or more first threshold values. In one or more exemplary monitor devices, to determine an operating state of the wound dressing is based on a second criteria set based on first parameter data and second parameter data of the parameter data, wherein the operating state is determined to be the second operating state if the second criteria set is satisfied. The second criteria set optionally comprises a second primary criterion based on the first parameter data, and a second secondary criterion based on the second parameter data. Applying first and second criteria set based on first parameter data and second parameter data allows for a distinction between different degrees and/or patterns of wetting.

In one or more exemplary monitor devices, to determine an operating state of the wound dressing is based on a second threshold set comprising one or more second threshold values.

In one or more exemplary monitor devices, to determine an operating state of the wound dressing is based on a default criteria set based on the parameter data, wherein the operating state is determined to be the default operating state if the default criteria set is satisfied, and optionally in accordance with a determination that the operating state is the default operating state, transmit a default monitor signal comprising monitor data indicative of the default operating state of the wound dressing. The default operating state may correspond to no wetting or a low degree of wetting of the (distal surface or side of) absorbent core layer.

In one or more exemplary monitor devices, to determine an operating state of the wound dressing is based on a third criteria set based on third parameter data of the parameter data, wherein the operating state is determined to be the third operating state if the third criteria set is satisfied. The third operating state of the wound dressing may correspond to a situation wherein the absorbent core layer is wetted to a third degree on the distal surface of the absorbent core layer and/or wherein a third wetting pattern is detected on the distal surface of the absorbent core layer.

The monitor device is optionally configured to, in accordance with a determination that the operating state is the third operating state, transmit a third monitor signal comprising monitor data indicative of the third operating state of the wound dressing.

The parameter data may be indicative of resistance between the two electrodes of an electrode pair forming a sensor point. For example, the first parameter data, the second parameter data, and the third parameter data, may be indicative of resistance between first electrode pair of the first sensor point, second electrode pair of the second sensor point, and third electrode pair of the third sensor point, respectively. Wetting of the distal surface of the absorbent core layer with exudate, i.e. exudate from the wound being absorbed by the absorbent core layer, is detected by a reduced resistance between the two electrodes of the sensor point(s). The sensor points are arranged or distributed along the distal surface of the absorbent core layer allowing the monitor device to detect and/or derive a degree of wetting and/or a wetting pattern or wetting distribution on the distal surface of the of the absorbent core layer.

In one or more exemplary monitor devices, the parameter data are indicative of a rate of change in resistance between the two electrodes of an electrode pair forming a sensor point. The first parameter data, the second parameter data, and the third parameter data may be indicative of a rate of change in resistance between first electrode pair of the first sensor point, second electrode pair of the second sensor point, and third electrode pair of the third sensor point, respectively. In one or more exemplary monitor devices, the first parameter data, the second parameter data, and the third parameter data may be indicative of a rate of change in voltage between the first electrode pair, the second electrode pair, and the third electrode pair, respectively. In one or more exemplary monitor devices, the first parameter data, the second parameter data, and the third parameter data may be indicative of a rate of change in current between the first electrode pair, the second electrode pair, and the third electrode pair, respectively.

In one or more exemplary monitor devices, the wound data comprises fourth wound data from a fourth sensor point of the wound dressing, and wherein to apply a processing scheme comprises to obtain fourth parameter data based on the fourth wound data and determine an operating state of the wound dressing based on the fourth parameter data.

The monitor device is optionally configured to, in accordance with a determination that the operating state is a fourth operating state, transmit a fourth monitor signal comprising monitor data indicative of the fourth operating state of the wound dressing. The fourth operating state of the wound dressing may correspond to a situation wherein the absorbent core layer is wetted to a fourth degree on the distal surface of the absorbent core layer and/or wherein a fourth wetting pattern is detected on the distal surface of the absorbent core layer.

In one or more exemplary monitor devices, to obtain parameter data comprises to obtain common parameter data of the parameter data based on a plurality of the first wound data, the second wound data, and the third wound data, and wherein to determine the operating state of the wound dressing is based on the common parameter data.

In one or more exemplary monitor devices, to determine an operating state comprises to determine a degree of wetting of the absorbent core layer, such as a degree of wetting of the distal side or surface of the absorbent core material. To determine a degree of wetting of the absorbent core material may comprising to determine if the degree of wetting satisfies first wetting criterion and/or if the degree of wetting satisfies second wetting criterion.

The monitor device is optionally configured to, in accordance with the degree of wetting satisfying first wetting criterion, setting the operating state to be the first operating state and optionally include the degree of wetting in the monitor data.

The monitor device is optionally configured to, in accordance with the degree of wetting satisfying a second wetting criterion, setting the operating state to be the second operating state and optionally include the degree of wetting in the monitor data.

In one or more exemplary monitor devices, to determine an operating state comprises to determine a wetting pattern of the absorbent core layer, such as a wetting pattern on the distal side or surface of the absorbent core material, and optionally to determine a pattern type of the wetting pattern from a plurality of pattern types. To determine a pattern type of the wetting pattern may comprise to determine if the wetting pattern satisfies first pattern type criterion, wherein the pattern type is determined as being a first pattern type if the first pattern type criterion is satisfied. To determine a pattern type of the wetting pattern may comprise to determine if the wetting pattern satisfies second pattern type criterion, wherein the pattern type is determined as being a second pattern type if the second pattern type criterion is satisfied.

The monitor device may be configured to, in accordance with the pattern type being a first pattern type, setting the operating state to be the first operating state and optionally including a pattern representation of the wetting pattern in the monitor data. The pattern representation may comprise a pattern type identifier and/or pattern data indicative of parameter data.

The monitor device may be configured to, in accordance with the pattern type being a second pattern type degree, setting the operating state to be the second operating state and optionally including a pattern representation of the wetting pattern in the monitor data. The pattern representation may comprise a pattern type identifier and/or pattern data indicative of parameter data.

The monitor device comprises a second interface connected to the processor. The second interface may comprise a loudspeaker connected to the processor, and wherein the processor is configured to transmit a monitor signal via the loudspeaker. In one or more exemplary monitor devices, the second interface comprises an antenna and a wireless transceiver, and wherein the processor is configured to transmit a monitor signal as a wireless monitor signal via the antenna and the wireless transceiver.

A wound dressing system is disclosed, the wound dressing system comprising a wound dressing and a monitor device, the wound dressing comprising an absorbent core layer, wherein the monitor device is a monitor device as described herein.

To obtain first parameter data based on the first wound data may comprise determining one or more first parameters based on the first wound data. To obtain second parameter data based on the second wound data may comprise determining one or more second parameters based on the second wound data. To obtain third parameter data based on the third wound data may comprise determining one or more third parameters based on the third wound data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

Parameter data, $P\_1, P\_2, \ldots, P\_N$, may comprise respective parameters $p\_1\_1, p\_2\_1, \ldots, p\_N\_1$ indicative of resistance between the respective two electrodes forming a sensor point of the wound dressing. Parameter data, $P\_1, P\_2, \ldots, P\_N$, may comprise respective parameters $p\_1\_2, p\_2\_2, \ldots, p\_N\_2$ each indicative of a rate of change in resistance between the respective two electrodes forming a sensor point of the wound dressing. Accordingly, $p\_1\_1$ of $P\_1$ may be the resistance measured between the first electrode $E\_1\_1$ and the second electrode $E\_2\_1$ forming the first sensor point $SP\_1\_1$, $p\_2\_1$ of $P\_2$ may be the resistance measured between first electrode $E\_1\_1$ and the second electrode $E\_2\_2$ forming the second sensor point $SP\_1\_2$.

In one or more exemplary monitor devices, to determine an operating state of the wound dressing is based on a first criteria set based on the first parameter data $P\_1$ ($p\_1\_1$) and/or one or more other parameter data $P\_2$ ($p\_2\_1$), $P\_3$ ($p\_3\_1$), $\ldots$, $P\_N$ ($p\_N\_1$), wherein the operating state is determined to be the first operating state if the first criteria set is satisfied. The first criteria set may comprise one or more first criteria based on one or more of $P\_1, P\_2, \ldots, P\_N$. The first criteria set may comprise a first primary criterion based on $P\_1$ ($p\_1\_1$). The first criteria set may comprise a first secondary criterion based on $P\_2$ ($p\_2\_1$). The first criteria set may comprise a first tertiary criterion based on $P\_3$ ($p\_3\_1$). The first criteria set may comprise N first criteria respectively based on $P\_1, P\_2, \ldots, P\_N$.

In one or more exemplary monitor devices, to determine an operating state of the wound dressing is based on a second criteria set based on the second parameter data $P\_2$ ($p\_2\_1$) and/or one or more other parameter data $P\_1$ ($p\_1\_1$), $P\_3$ ($p\_3\_1$), $\ldots$, $P\_N$ ($p\_N\_1$), wherein the operating state is determined to be the second operating state if the second criteria set is satisfied. The second criteria set may comprise one or more second criteria based on one or more of $P\_1, P\_2, \ldots, P\_N$. The second criteria set may comprise a second primary criterion based on $P\_1$ ($p\_1\_1$). The second criteria set may comprise a second secondary criterion based on $P\_2$ ($p\_2\_1$). The second criteria set may comprise a second tertiary criterion based on $P\_3$ ($p\_3\_1$). The second criteria set may comprise N second criteria respectively based on $P\_1, P\_2, \ldots, P\_N$.

In one or more exemplary monitor devices, to determine an operating state of the wound dressing may comprise to determine the number of parameters $p\_1\_1, p\_2\_1, \ldots, p\_N\_1$ having resistances less than a first threshold as a first common parameter of common parameter data. The operating state of the wound dressing may be based on the number of parameters $p\_1\_1, p\_2\_1, \ldots, p\_N\_1$ having resistances less than a first threshold. The operating state of the wound dressing may be determined as the first operating state if the first common parameter being the number of parameters $p\_1\_1, p\_2\_1, \ldots, p\_N\_1$ having resistances less than a first threshold is in a first range, e.g. from 0.25 N to 0.5 N. The first operating state may be indicative of a low-wetted absorbent core layer, i.e. a high degree of remaining absorbent capacity of the wound dressing/absorbent core layer. The operating state of the wound dressing may be determined as the second operating state if the first common parameter being the number of parameters $p\_1\_1, p\_2\_1, \ldots, p\_N\_1$ having resistances less than a first threshold is in a second range, e.g. from 0.5 N to 0.75 N. The second operating state may be indicative of a medium-wetted absorbent core layer, i.e. a medium degree of remaining absorbent capacity of the wound dressing/absorbent core layer.

The operating state of the wound dressing may be determined as a default operating state if the first common parameter being the number of parameters $p\_1\_1, p\_2\_1, \ldots, p\_N\_1$ having resistances less than a first threshold is less than a default threshold. The default threshold may be a fixed value or based on the number N of sensor points. The default threshold may be 0.1 N or 0.25 N. The processor is optionally configured to, in accordance with a determination that the operating state is the default operating state, transmit a default monitor signal comprising monitor data indicative of the default operating state of the wound dressing. The default operating state may be indicative of a substantially non-wetted absorbent core layer, i.e. a very high degree of remaining absorbent capacity of the wound dressing/absorbent core layer.

In one or more exemplary monitor devices, to determine an operating state of the wound dressing is based on a default criteria set based on parameter data $P\_1, P\_2, \ldots, P\_N$, wherein the operating state is determined to be the default operating state if the default criteria set is satisfied, and in accordance with a determination that the operating state is the default operating state, transmit a default monitor signal comprising monitor data indicative of the default operating state of the wound dressing.

In one or more exemplary monitor devices, to determine an operating state of the wound dressing is based on a third criteria set based on parameter data $P\_1, P\_2, \ldots, P\_N$, wherein the operating state is determined to be the third operating state if the third criteria set is satisfied. The operating state of the wound dressing may be determined as the third operating state if the first common parameter being the number of parameters $p\_1\_1, p\_2\_1, \ldots, p\_N\_1$ having resistances less than a first threshold is in a third range, e.g. from 0.75 N to 0.9 N.

The processor is optionally configured to, in accordance with a determination that the operating state is the third operating state, transmit a third monitor signal comprising monitor data indicative of the third operating state of the wound dressing. In one or more exemplary monitor devices, the third operating state of the wound dressing corresponds to a situation wherein the absorbent core layer is wetted to a third degree on the distal surface. The third degree may be indicative of low degree of remaining absorbent capacity of the wound dressing/absorbent core layer.

In one or more exemplary monitor devices, to determine an operating state of the wound dressing is based on a fourth criteria set based on parameter data $P\_1, P\_2, \ldots, P\_N$, wherein the operating state is determined to be the fourth operating state if the fourth criteria set is satisfied. The operating state of the wound dressing may be determined as the fourth operating state if the first common parameter being the number of parameters $p\_1\_1, p\_2\_1, \ldots, p\_N\_1$ having resistances less than a first threshold is in a fourth range, e.g. from 0.9 N to N.

The processor is optionally configured to, in accordance with a determination that the operating state is the fourth operating state, transmit a fourth monitor signal comprising monitor data indicative of the fourth operating state of the wound dressing. In one or more exemplary monitor devices, the fourth operating state of the wound dressing corresponds to a situation wherein the absorbent core layer is wetted to a fourth degree on the distal surface. The fourth degree may be indicative of very low or no degree of remaining absorbent capacity of the wound dressing/absorbent core layer.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as a wound dressing interface for electrically and/or mechanically connecting the monitor device to the wound dressing. Thus, the wound dressing interface is configured to electrically and/or mechanically couple the monitor device and the wound dressing. The first interface may be configured as an accessory device interface for electrically and/or mechanically connecting the monitor device to an accessory device. The first interface may be configured for coupling to a docking station of the wound dressing system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the wound dressing. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 16.

The first interface of the monitor device may comprise a coupling part for forming a mechanical connection, such as a releasable coupling between the monitor device and the wound dressing. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensors. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

The wound dressing system may comprise a docking station forming an accessory device of the wound dressing system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

The method may comprise mechanically and electrically coupling the first interface to a monitor interface of the wound dressing.

FIG. 1 illustrates an exemplary wound dressing system. The wound dressing system 1 comprises a wound dressing 2, a monitor device 4, and optionally an accessory device 6 (e.g., a mobile telephone). The monitor device 4 is connectable to the wound dressing 2 via respective first connectors of the monitor device 4 and wound dressing 2. The monitor device 4 is configured for wireless communication with the accessory device 6. Optionally, the accessory device 6 is configured to communicate with a server device 8 of the wound dressing system 1, e.g. via network 10. The server device 8 may be operated and/or controlled by the wound dressing manufacturer and/or a service centre. Wound data and/or parameter data based on the wound data are obtained from electrodes/sensors of the wound dressing 2 with the monitor device 4. The monitor device 4 processes the wound data and/or parameter data based on the wound data to determine monitor data that are transmitted to the accessory device 6. In the illustrated wound dressing system, the accessory device 6 is a mobile phone; however, the accessory device 6 may be embodied as another handheld device, such as a tablet device, or a wearable, such as a watch or other wrist-worn electronic device. Accordingly, the monitor device 4 is configured to determine and transmit monitor data to the accessory device 6.

The wound dressing system 1 optionally comprises a docking station 20 forming an accessory device of the wound dressing system 1. The docking station comprises 20 comprises a docking monitor interface including a first connector 22 configured for electrically and/or mechanically connecting the monitor device 4 to the docking station 20. The docking monitor interface may be configured for wirelessly connecting the monitor device 4 to the docking station 20. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

A user interface refers herein to a graphical representation comprising a collection of user interface objects. A user interface comprises one or more user interface objects. A user interface may be referred to as a user interface screen.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be a mini-application that may be used by the user and created by the user. A user interface object may comprise a prompt, application launch icon, and/or an action menu. An input, such as first input and/or second input, may comprise a touch (e.g. a tap, a force touch, a long press), and/or a movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

The display of the accessory device may be configured to detect touch (e.g. the display is a touch-sensitive display), the input comprises a contact on the touch sensitive display.

A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all the visual output may be seen as corresponding to user-interface objects.

The processor of the accessory device may be configured to display, on the display, one or more user interfaces, such as user interface screens, including a first user interface and/or a second user interface. A user interface may comprise one or more, such as a plurality of user interface objects. For example, the first user interface may comprise a first primary user interface object and/or a first secondary user interface object. A second user interface may comprise a second primary user interface object and/or a second secondary user interface object. A user interface object, such as the first primary user interface object and/or the second primary user interface object, may represent an operating state of the wound dressing.

Figure 2:
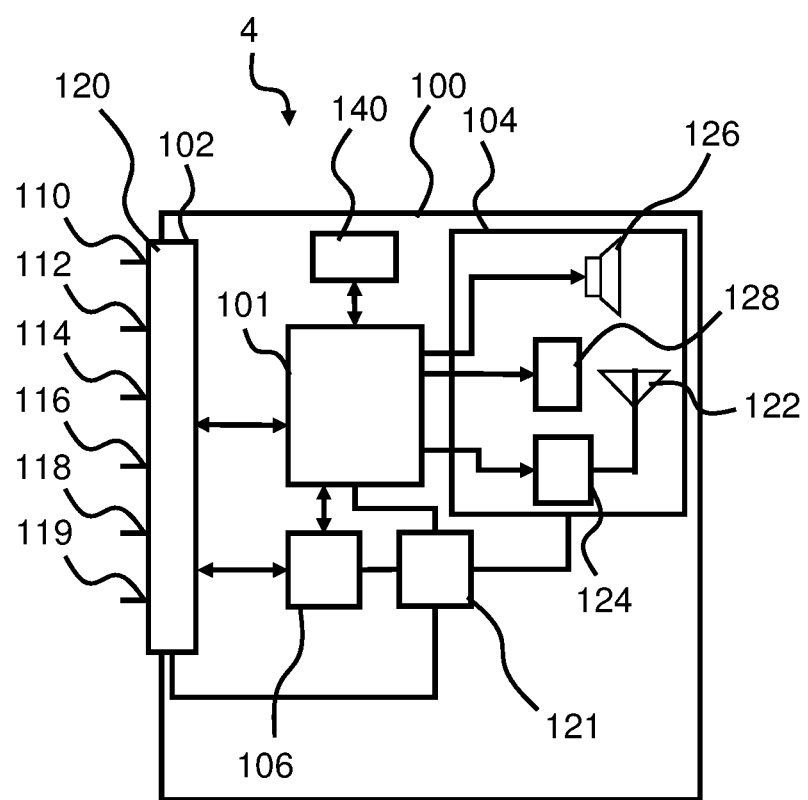
FIG. 2 illustrates an exemplary monitor device of the wound dressing system.

FIG. 2 is a schematic block diagram of an exemplary monitor device 4. The monitor device 4 comprises a monitor device housing 100, a processor 101, and one or more interfaces, the one or more interfaces including a first interface 102 (wound dressing interface) and a second interface 104 (accessory interface). The monitor device 4 comprises a memory 106 for storing wound data and/or parameter data based on the wound data. The memory 106 is connected to the processor 101 and/or the first interface 102. The first interface 102 is configured as a wound dressing interface for electrically and/or mechanically connecting the monitor device 4 to the wound dressing, e.g. wound dressing 2. The first interface 102 comprises a plurality of terminals for forming electrical connections with respective terminals of the wound dressing. The first interface 102 comprises a first terminal 110, a second terminal 112 and a third terminal 114. The first interface 102 optionally comprises a fourth terminal 116, a fifth terminal 118 and/or sixth terminal 119. The first interface 102 of the monitor device 4 comprises a coupling part 120 for forming a mechanical connection, such as a releasable coupling, between the monitor device 4 and the wound dressing. The coupling part 120 and terminals 110, 112, 114, 116, 118, 119 of the first interface 102 form (at least part of) a first connector of the monitor device 4. Terminals 110, 112, and 114 may be respectively coupled to first electrodes 210A, 210B, 210C via the monitor interface of the wound dressing, and terminals 116, 118, 119 may be respectively coupled to second electrodes 212A, 212B, 212C via the monitor interface of the wound dressing.

The monitor device 4 comprises a power unit 121 for powering the monitor device and active components thereof, i.e. the power unit 121 is connected to the processor 101, the first interface 102, the second interface 104, and memory 106. The power unit comprises a battery and optionally charging circuitry. The charging circuitry is optionally connected to the battery and terminals of the first interface 102 for charging the battery via terminals of the first interface, e.g. terminals of the first connector.

The second interface 104 of monitor device 4 is configured as an accessory interface for connecting the monitor device 4 to one or more accessory devices such as accessory device 6. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. The sensor unit 140 comprises a temperature sensor for feeding temperature data to the processor and/or a G-sensor or accelerometer for feeding acceleration data to the processor 101.

The processor 101 is configured to apply a processing scheme, and the first interface 102 is configured for collecting wound data from the wound dressing coupled to the first interface, the wound data comprising wound data from sensor points (electrode pairs) of the wound dressing. The wound data may comprise first wound data WD_1 from a first electrode pair (first sensor point) of the wound dressing, second wound data WD_2 from a second electrode pair (second sensor point) of the wound dressing, and third wound data WD_3 from a third electrode pair (third sensor point) of the wound dressing. In the illustrated monitor device, the processor is configured to collect, WD_1, WD_2, WD_3, . . . , WD_9 from nine sensor points of the wound dressing formed by nine electrode pairs being combinations of a first electrode of the first set of first electrodes and a second electrode of the second set of second electrodes. The wound data may be stored in the memory 106 and/or processed in the processor 101 in order to obtain parameter data based on the wound data. The parameter data may be stored in the memory 106. The processor 101 is configured to apply a processing scheme, wherein to apply a processing scheme comprises obtain first parameter data P_1 including p_1_1 being the resistance between the two electrodes forming the first sensor point based on the first wound data; obtain second parameter data P_2 including p_2_1 being the resistance between the two electrodes forming the second sensor point based on the second wound data; obtain third parameter data P_3 including p_3_1 being the resistance between the two electrodes forming the third sensor point based on the third wound data. In other words, the processor 101 is configured to obtain parameters p_1_1, p_2_1, . . . , p_9_1 being resistances based on respective wound data WD_1, WD_2, . . . , WD_9 obtained between the two electrodes forming the respective sensor points. To apply a processing scheme comprises to determine an operating state of the wound dressing based on one or more, e.g. all, of the parameter data P_1, P_2, . . . , P_9 including p_1_1, p_2_1, . . . , p_9_1. The operating state is optionally indicative of a degree of wetting or wetting pattern on the distal side of the absorbent core layer of the wound dressing.

The monitor device 4 is optionally configured to, in accordance with a determination that the operating state is a first operating state of the wound dressing, transmit a first monitor signal comprising monitor data indicative of the first operating state of the wound dressing via the second interface, the monitor data optionally including including a pattern representation of the wetting pattern and/or the degree of wetting. The pattern representation may comprise a pattern type identifier and/or pattern data indicative of or comprising parameter data. Optionally, the monitor device 4 may be configured to, in accordance with a determination that the operating state is a second operating state of the wound dressing, transmit a second monitor signal comprising monitor data indicative of the second operating state of the wound dressing via the second interface, the monitor data optionally including including a pattern representation of the wetting pattern and/or the degree of wetting. The pattern representation may comprise a pattern type identifier and/or pattern data indicative of or comprising parameter data.

Figure 3:
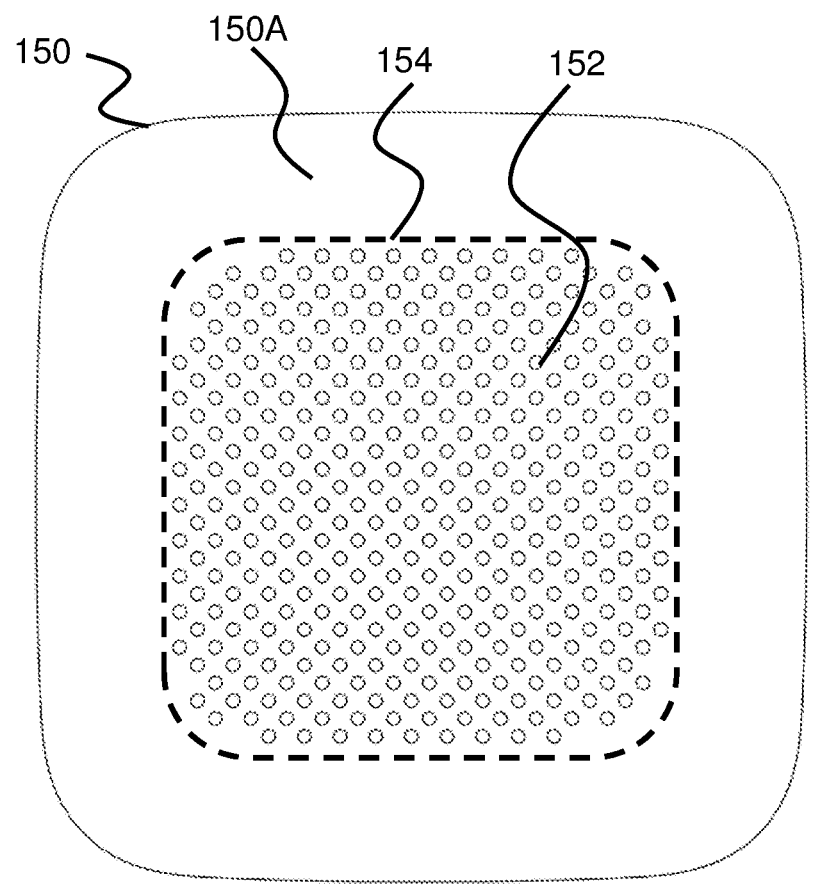
FIG. 3 is a proximal view of a first adhesive layer of a wound dressing.

FIG. 3 shows a proximal view of an exemplary first adhesive layer of the wound dressing. The first adhesive layer 150 has a proximal surface 150A configured for attachment of the wound dressing to the skin surface of a user. The first adhesive layer has perforations or through-going openings 152 arranged within absorbing region 154 for allowing exudate from the wound to flow through the perforations of first adhesive layer 150 to be absorbed by absorbent core layer arranged on the distal side of the first adhesive layer.

Figure 4:
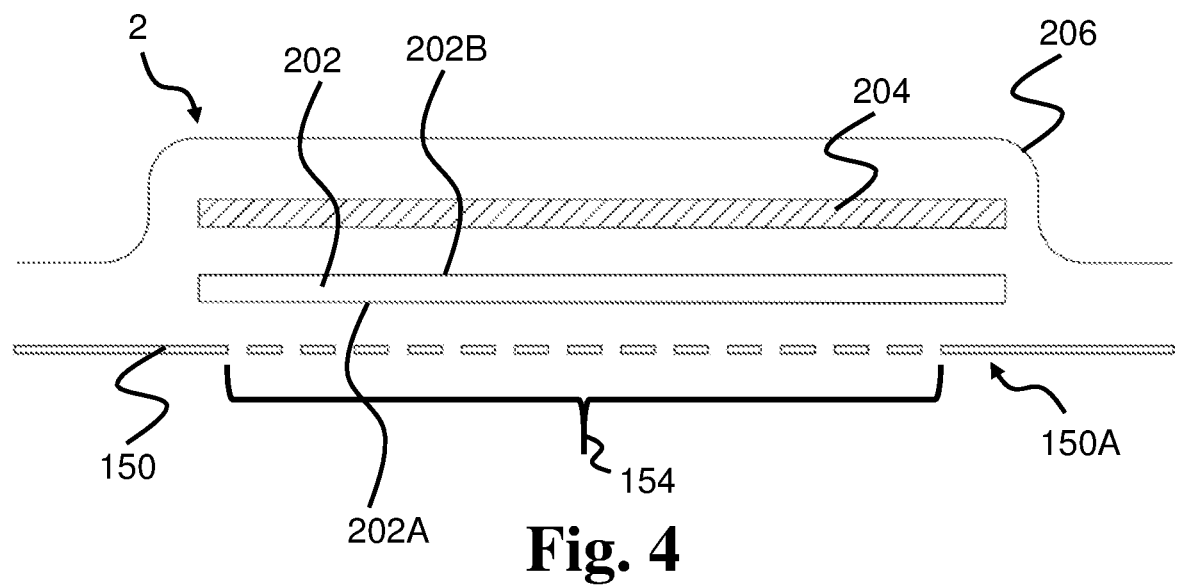
FIG. 4 is a schematic cross-section of an exemplary wound dressing.

FIG. 4 is a schematic cross-section of an exemplary wound dressing. The wound dressing 2 comprises a first adhesive layer 150 with a proximal surface 150A configured for attachment of the wound dressing to the skin surface of a user. The wound dressing 2 may form part of wound dressing system 1. The wound dressing 2 comprises an absorbent core layer 202 with a proximal surface 202A and a distal surface 202B; an electrode assembly 204 comprising a plurality of electrodes arranged on a distal side of the absorbent core layer 202; and a top layer 206 at least partly on a distal side of the electrode assembly.

Figure 5:
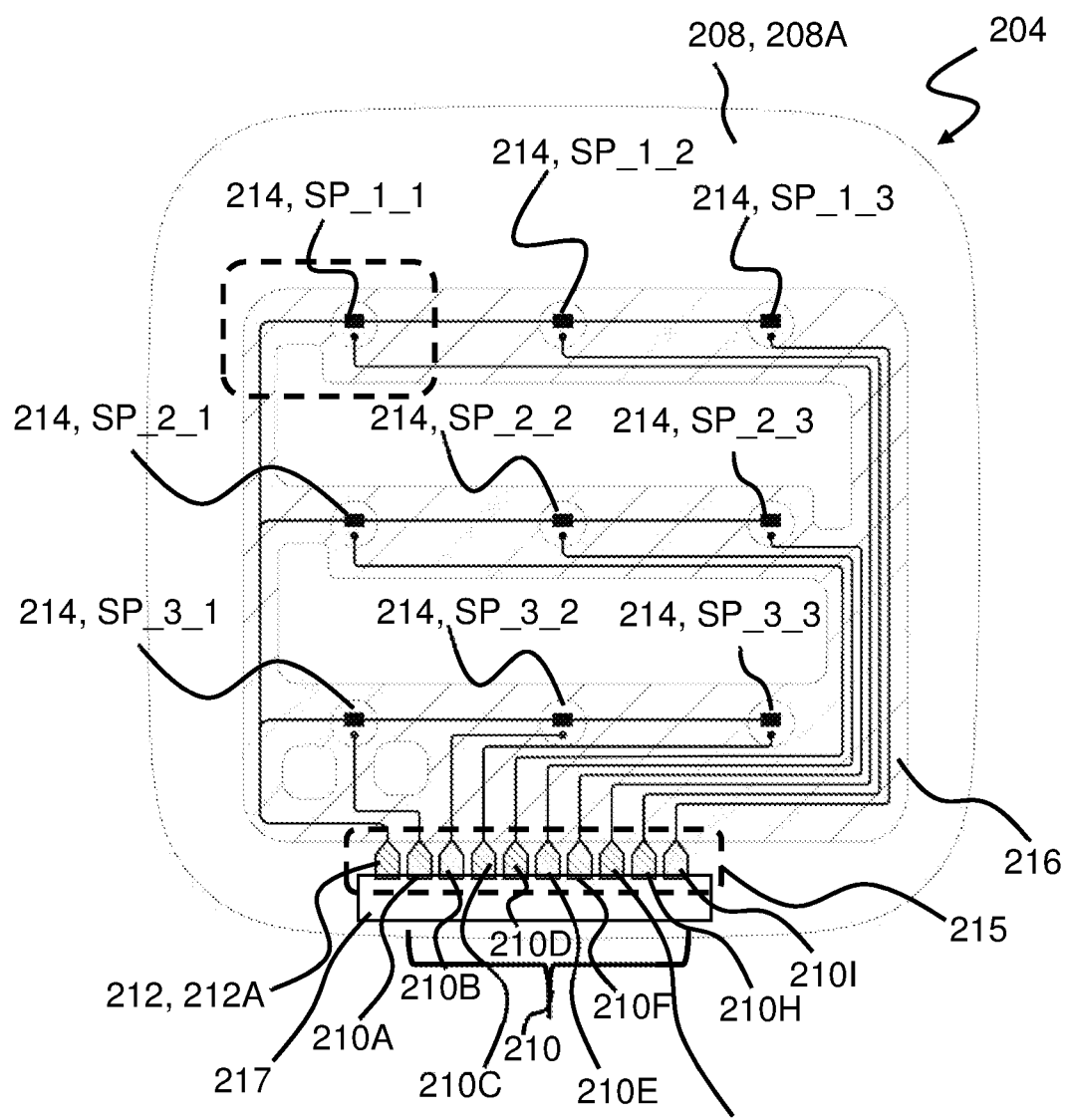
FIG. 5 is a proximal view of an exemplary electrode assembly.

FIG. 5 is a proximal view of an exemplary and schematic electrode assembly of wound dressing 2. The electrode assembly 204 comprises a first support layer 208 and a plurality of electrodes printed on a proximal surface 208A of the first support layer, i.e. the plurality of electrodes is arranged on a distal side of the absorbent core layer of the wound dressing. 202. The plurality of electrodes comprises a first set 210 of nine first electrodes 210A, . . . , 210I and a second set 212 of a second electrode 212A. A sensing part of a first electrode and a sensing part of a second electrode forms a sensor point. The electrode assembly 204 comprises nine sensor points 214 arranged on the proximal surface of the first support layer and distributed along a distal surface of the absorbent core layer, e.g. as shown with nine sensor points arranged in a 3×3 matrix sensor point configuration.

The electrode assembly 204 comprises a first masking layer 216 covering and isolating electrode parts of the first electrodes 210A, . . . , 210I and the second electrode 212A. The first masking layer 216 is printed on the first support layer/electrodes and comprises a number of sensor point openings to form respective sensor points of the electrode assembly by exposing sensing parts of first electrodes 210A, . . . , 210I and second electrode 212A.

The second electrode 212A operates as a reference electrode (ground) for the first electrodes 210A, . . . , 210I and forms a part of the respective sensor points 214 of electrode assembly 204. The sensor points 214 are arranged with a distance between two neighbouring sensor points in the range from 3 mm to 50 mm, e.g. with a center-to-center distance of 30 mm.

Each electrode 210A, . . . , 210I, 212 has a respective connection part (connection parts indicated with dashed box 215 for forming a connection to monitor device via a wired or wireless monitor interface of the wound dressing.

The electrode assembly 204 comprises a multiplexer 217 coupled to the connection parts included in the dashed box 215. The multiplexer 217 connects the connection parts of the electrodes 210A, . . . , 210I, 212 to respective terminals 110, 112, 114, 116, 118, 119 of the first interface 102 of the monitor device 4. The monitor device 4 can select a desired multiplexer configuration of the multiplexer 217 by sending one or more control signals to the multiplexer 217, as described in relation to FIG. 16. While the multiplexer 217 is depicted as being embedded in the electrode assembly 204 in alternative embodiments, the multiplexer 217 is embedded in the coupling part 120.

Figure 6:
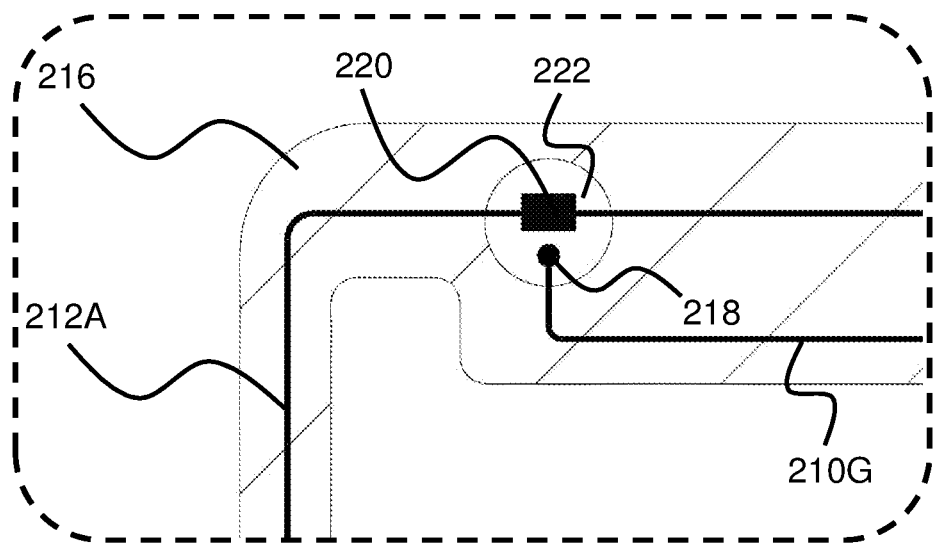
FIG. 6 is more detailed proximal view of a part of exemplary electrode assembly of FIG. 5.

FIG. 6 shows a more detailed view of a sensor point 214 of an electrode assembly, e.g. electrode assembly 204, see dashed box in FIG. 5. The sensor point 214 is formed by a first sensing part 218 of a first electrode and a second sensing part 220 of a second electrode. The first sensing part 218 and the second sensing part 220 are exposed to the absorbent core layer of the wound dressing through sensor point opening 222 of the first masking layer 216. Thus, exudate or other fluid reaching the distal surface of the absorbent core layer short-circuits the first sensing part 218 and the second sensing part 220. In the illustrated electrode assembly, the sensor point opening 222 is circular with a radius in the range from 2 to 10 mm.

Figure 7:
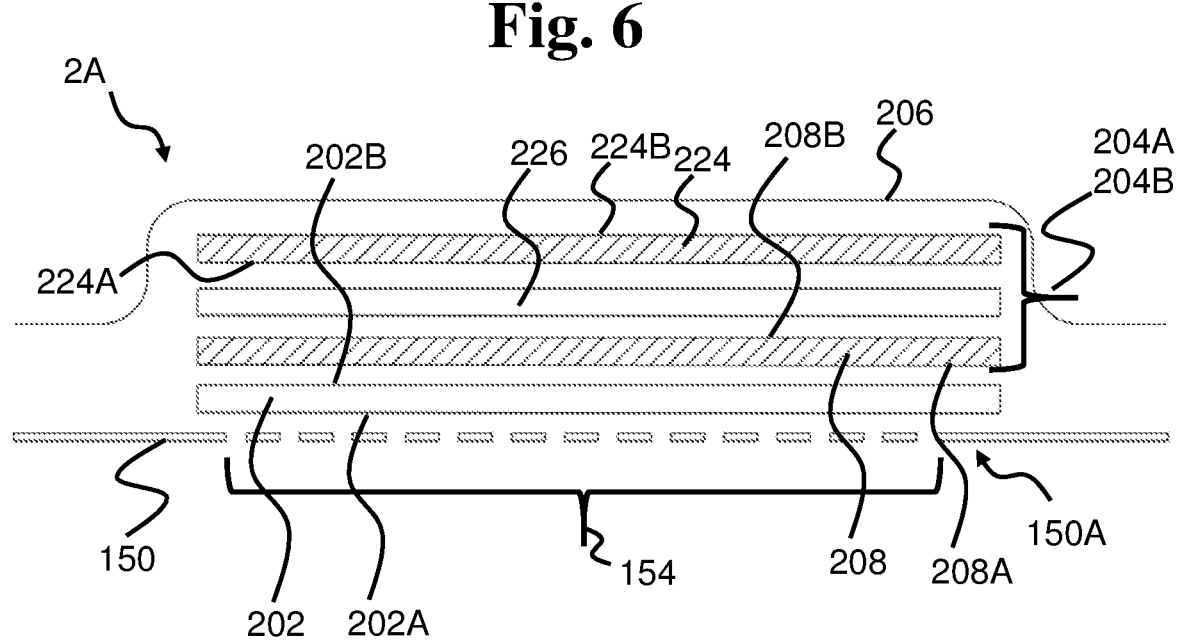
FIG. 7 is a schematic cross-section of an exemplary wound dressing.

FIG. 7 is a schematic cross-section of an exemplary wound dressing 2A. The wound dressing 2A comprises a first adhesive layer 150 with a proximal surface 150A configured for attachment of the wound dressing to the skin surface of a user. The wound dressing 2A may form part of wound dressing system 1. The wound dressing 2A comprises an absorbent core layer 202 with a proximal surface 202A and a distal surface 202B; and an electrode assembly 204 comprising a plurality of electrodes arranged on a distal side of the absorbent core layer 202, wherein the plurality of electrodes comprises a first set of first electrodes arranged on a proximal surface 208A and/or distal surface 208B of first support layer 208. The electrode assembly 204A comprises a second support layer 224, and the plurality of electrodes comprises a second set of second electrodes arranged on a proximal surface and/or distal surface of second support layer 208. The electrode assembly 204A comprises a spacing layer 226 arranged between the first support layer 208 and the second support layer 224. Further, a top layer 206 is arranged at least partly on a distal side of the electrode assembly 204A.

Figure 8:
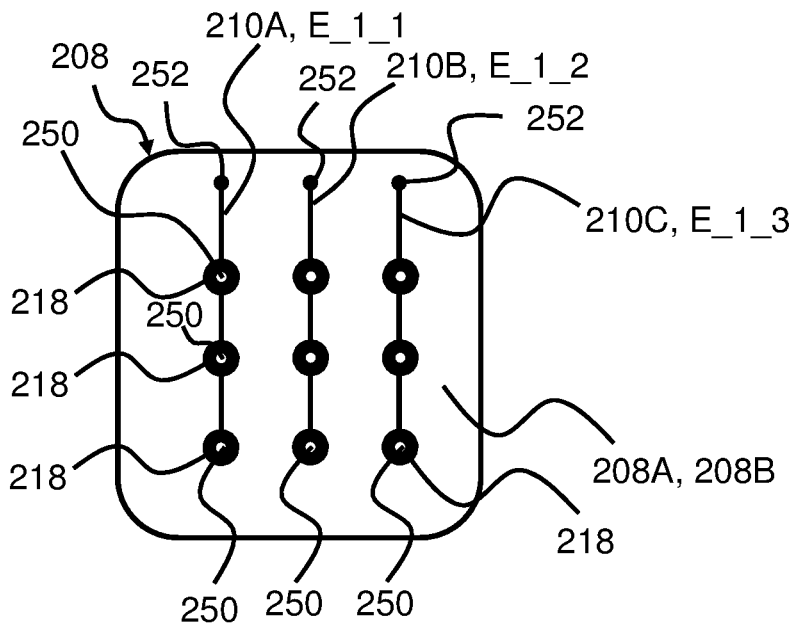
FIG. 8 is a proximal view of an exemplary first support layer.

FIG. 8 shows a proximal view of an exemplary first support layer 208, e.g. of electrode assembly 204, electrode assembly 204A, electrode assembly 204B. The electrode assembly comprises three first electrodes 210A, 210B, 210C printed on the proximal surface 208A of the first support layer 208, wherein each electrode 210A, 210B, 210C comprises three first sensing parts 218 exposed through respective sensor point openings of first masking layer, see FIG. 9. The first support layer 208 has a plurality of sensor point openings 250 for allowing exudate to pass through the first support layer (from proximal side to distal side) and reach sensing parts of second electrodes arranged on the distal side or distal surface of the first support layer 208. Each sensor point opening 250 is optionally centred in a respective first sensing part 218 of a first electrode. Each first electrode 210A, 210B, and 210C has a connection part 252 for connection to or forming part of a monitor interface of the wound dressing. In one or more exemplary electrode assemblies, e.g. electrode assemblies 204A, 204B shown in FIG. 7, the first electrodes 210A, 210B, 210C may be printed on the distal surface 208B of the first support layer 208.

Figure 9:
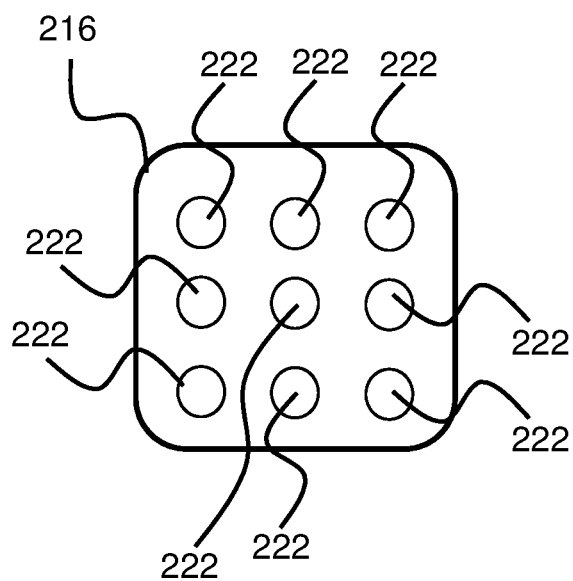
FIG. 9 is a proximal view of an exemplary first masking layer.

FIG. 9 shows a proximal view of an exemplary first masking layer 216 of electrode assembly with first support layer of FIG. 8. The first masking layer 216 is printed on the proximal surface/distal surface of first support layer partly covering first electrodes 210A, 210B, and 210C of the electrode assembly. The first masking layer comprises nine sensor point openings 222 arranged to fit a 3×3 matrix sensor point configuration and respectively aligned with first sensing parts 218 of first electrodes 210A, 210B, 210C.

Figure 10:
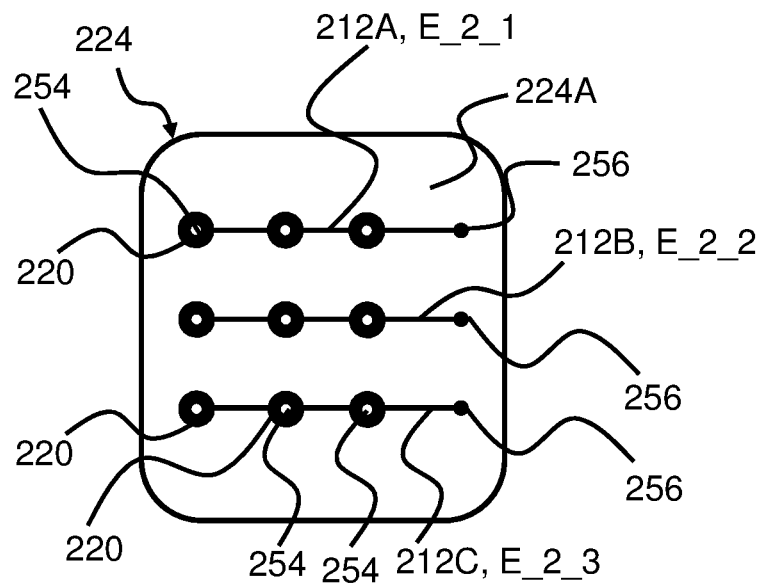
FIG. 10 is a proximal view of an exemplary second support layer.

FIG. 10 shows a proximal view of an exemplary second support layer 224, e.g. of electrode assembly 204A. The electrode assembly comprises three second electrodes 212A, 212B, 212C printed on proximal surface 224A of the second support layer 224, wherein each electrode 212A, 212B, 212C comprises three second sensing parts 220 exposed through respective sensor point openings of second masking layer, see FIG. 11. Optionally, the second support layer 224 has a plurality of sensor point openings 254 for allowing exudate to pass through the second support layer (from proximal side to distal side). Each sensor point opening 254 is optionally centred in a respective second sensing part 220 of a second electrode. Each second electrode 212A, 212B, and 212C has a connection part 256 for connection to or forming part of a monitor interface of the wound dressing.

Figure 11:
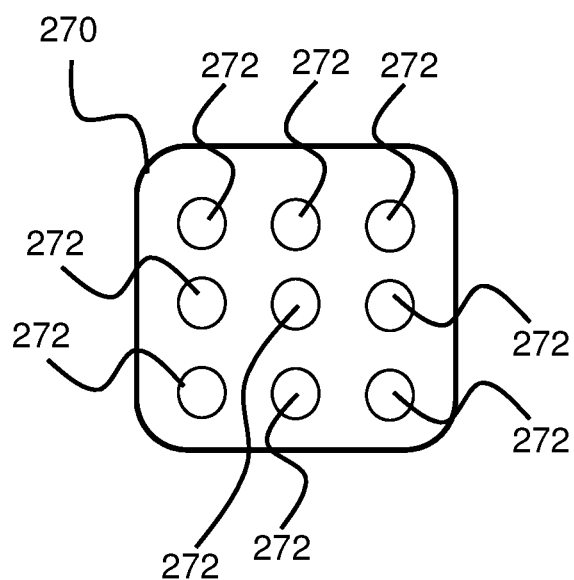
FIG. 11 is a proximal view of an exemplary second masking layer.

FIG. 11 shows a proximal view of an exemplary second masking layer 270 of electrode assembly 204A. The second masking layer 270 is printed on the proximal surface 224A of the second support layer 224 partly covering second electrodes 212A, 212B, and 212C of the electrode assembly. The second masking layer 270 comprises nine sensor point openings 272 arranged to fit a 3×3 matrix sensor point configuration and respectively aligned with second sensing parts 220 of second electrodes 212A, 212B, 212C. Referring back to FIGS. 7-11, the first sensing parts 218 of first electrodes 210A, 210B, 210C are respectively aligned with a second sensing part 220 of second electrodes 212A, 212B, 212C to form sensor points.

Figure 12:
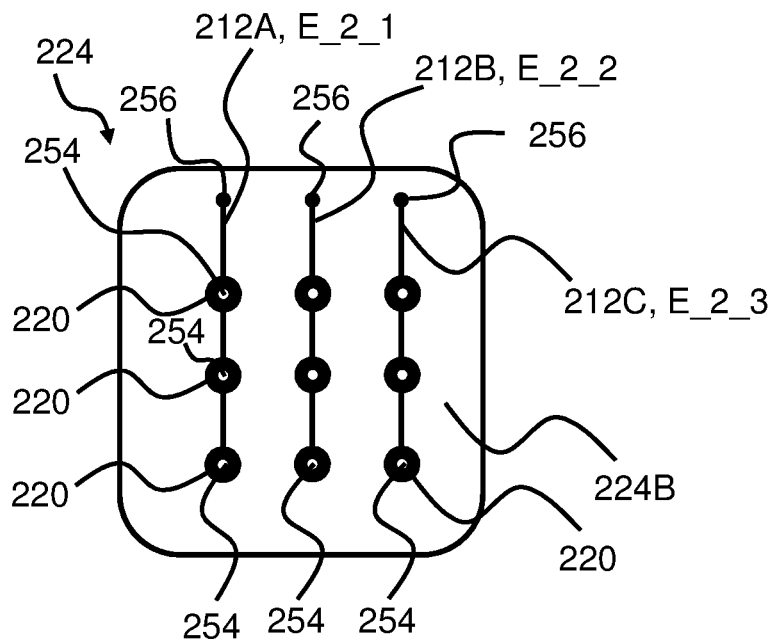
FIG. 12 is a distal view of an exemplary second support layer.

FIG. 12 shows a distal view of an exemplary second support layer 224, e.g. of electrode assembly 204B. The electrode assembly comprises three second electrodes 212A, 212B, 212C printed on distal surface 224B of the second support layer 224, wherein each electrode 212A, 212B, 212C comprises three second sensing parts 220 optionally exposed through respective sensor point openings of second masking layer, see FIG. 13. The second support layer 224 has a plurality of sensor point openings 254 for allowing exudate to pass through the second support layer (from proximal side to distal side) and reach second sensing parts 220 of second electrodes arranged on the distal side or distal surface of the second support layer 224. Each sensor point opening 254 is optionally centred in a respective second sensing part 220 of a second electrode. Each second electrode 212A, 212B, and 212C has a connection part 256 for connection to or forming part of a monitor interface of the wound dressing.

Figure 13:
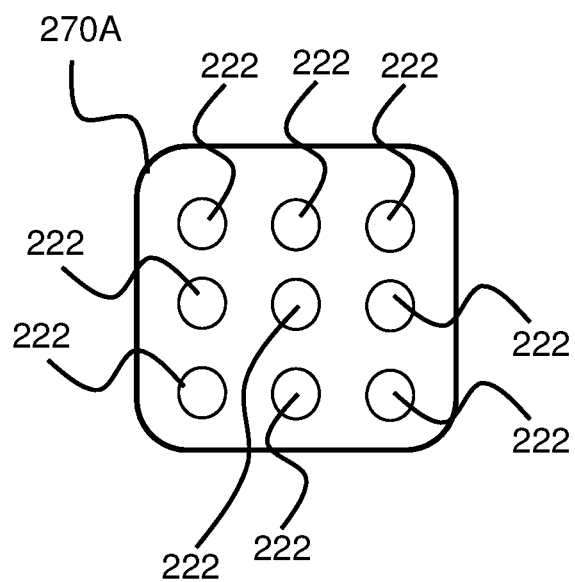
FIG. 13 is a proximal view of an exemplary second masking layer.

FIG. 13 shows a proximal view of an exemplary and optional second masking layer 270A of electrode assembly 204B or a second masking layer 270A of electrode assembly 204. The second masking layer 270A is printed on the distal surface 224B of the second support layer 224 or on distal surface 208B of the first support layer 208 partly covering second electrodes 212A, 212B, and 212C of the electrode assembly. The second masking layer 270A comprises nine sensor point openings 272 arranged to fit a 3×3 matrix sensor point configuration and respectively aligned with second sensing parts 220 of second electrodes 212A, 212B, 212C. Referring back to FIGS. 4 and 7-11, the first sensing parts 218 of first electrodes 210A, 210B, 210C are respectively aligned with a second sensing part 220 of second electrodes 212A, 212B, 212C to form sensor points.

Figure 14:
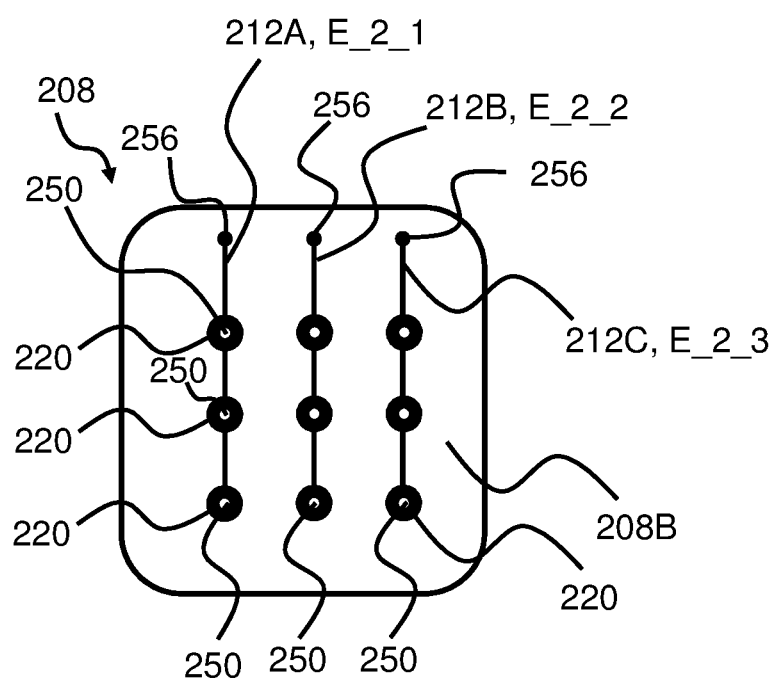
FIG. 14 is a distal view of an exemplary first support layer.

FIG. 14 shows a distal view of an exemplary first support layer 208 of an electrode assembly, e.g. of electrode assembly 204. The electrode assembly comprises three second electrodes 212A, 212B, 212C printed on distal surface 224B of the first support layer 208, wherein each second electrode 212A, 212B, 212C comprises three second sensing parts 220 optionally exposed through respective sensor point openings of second masking layer, see FIG. 13. The first support layer 208 has a plurality of sensor point openings 250 for allowing exudate to pass through the first support layer (from proximal side to distal side) and reach second sensing parts 220 of second electrodes arranged on the distal side or distal surface of the first support layer 208. Each sensor point opening 250 is optionally centred in a respective second sensing part 220 of a second electrode. Each second electrode 212A, 212B, and 212C has a connection part 256 for connection to or forming part of a monitor interface of the wound dressing.

Figure 15:
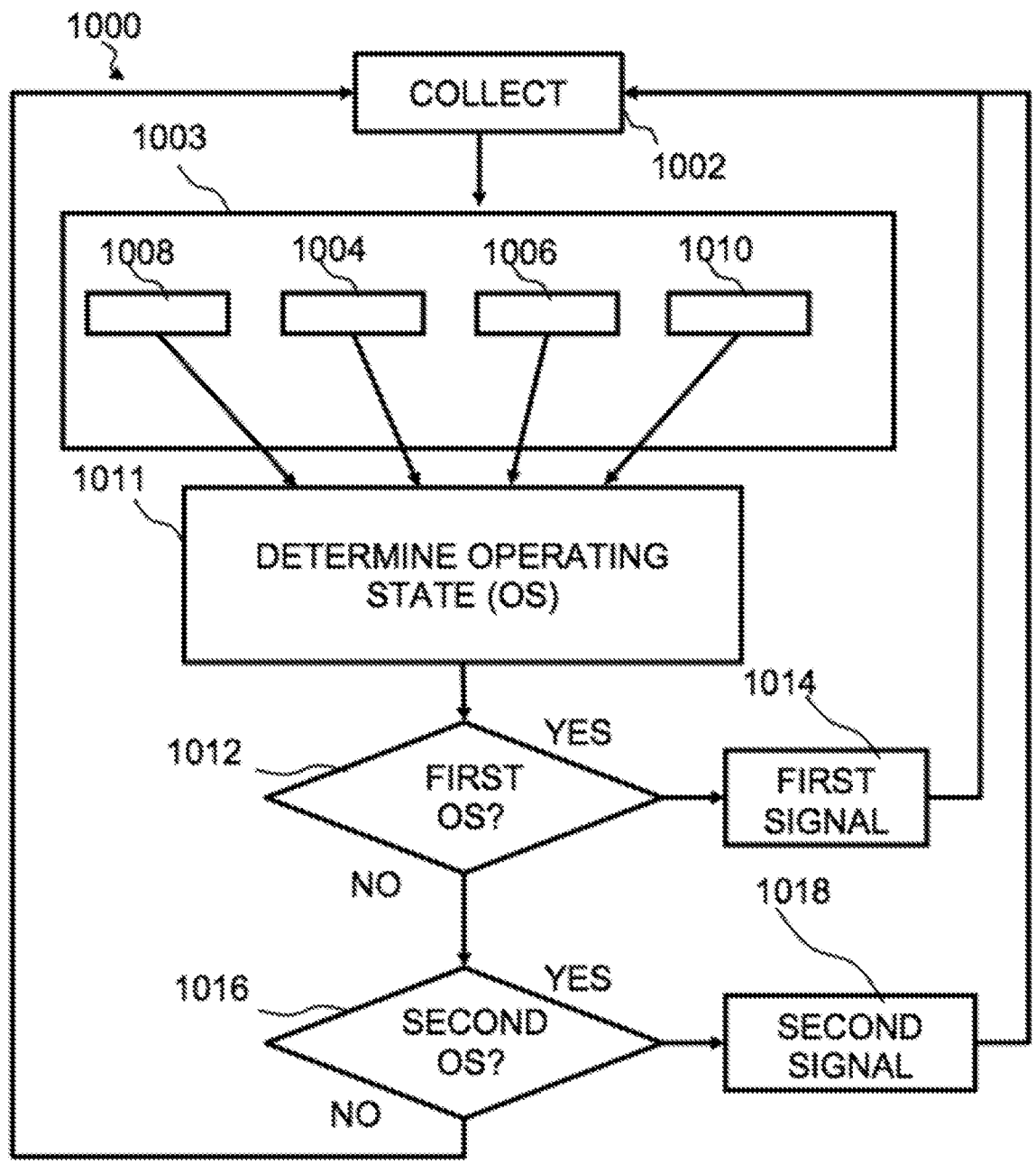
FIG. 15 is a flow chart of an exemplary method of monitoring a wound dressing.

FIG. 15 shows a flow chart of an exemplary method of monitoring a wound dressing comprising an absorbent core layer. The method 1000 comprises, at a monitor device comprising a processor configured to apply a processing scheme; memory; a first interface connected to the processor and the memory; and a second interface connected to the processor, collecting 1002 wound data from the wound dressing, the wound data comprising first wound data from a first sensor point of the wound dressing, second wound data from a second sensor point of the wound dressing, and third wound data from a third sensor point of the wound dressing; applying a processing scheme comprising obtaining 1003 parameter data based on the wound data; and determining 1011 an operating state of the wound dressing based on the parameter data, wherein the operating state is indicative of wetting of the absorbent core layer of the wound dressing; in accordance 1012 with a determination that the operating state is a first operating state, transmitting 1014 a first monitor signal comprising monitor data indicative of the first operating state of the wound dressing via the second interface; and
in accordance 1016 with a determination that the operating state is a second operating state, transmitting a second monitor signal comprising monitor data indicative of the second operating state of the wound dressing via the second interface. Obtaining 1003 parameter data optionally comprises obtaining 1004 first parameter data based on first wound data and indicative of resistance between two electrodes of a first sensor point, obtaining 1006 second parameter data based on second wound data and indicative of resistance between two electrodes of a second sensor point, obtaining 1008 third parameter data based on third wound data and indicative of resistance between two electrodes of a third sensor point, and obtaining 1010 fourth parameter data based on fourth wound data and indicative of resistance between two electrodes of a fourth sensor point.

Figure 16:
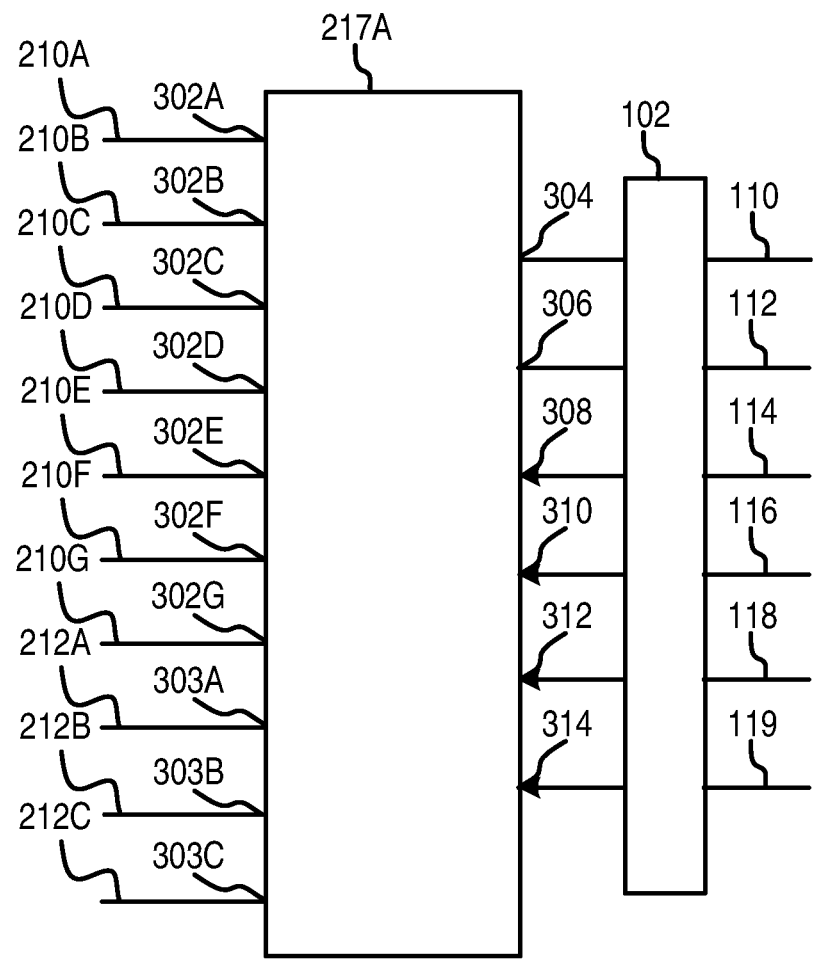
FIG. 16 is a distal view of a part of a wound dressing including a multiplexer and monitor interface.

FIG. 16 schematically shows a part of an exemplary wound dressing 2B including the multiplexer 217A and a monitor interface 102. The wound dressing 2B comprises a first set of first electrodes including electrodes 210A, . . . , 210G and a second set of second electrodes including electrodes 212A, . . . , 212C. Each of the electrodes 210A, . . . , 210G, 212A, . . . , 212C is connected to a respective input pin 302A, . . . , 302G, 303A, . . . , 303C of N input pins included in the multiplexer 217A. That is, each electrode of the first set of first electrodes is connected to a respective input pin of a first set of first input pins 302A, . . . , 302G and each electrode of the second set of second electrodes is connected to a respective input pin of a second set of second input pins 303A, . . . , 303C.

For example, in the configuration shown, a first primary electrode 210A of the first set of first electrodes 210A, . . . , 210G is connected to a first primary input pin 302A of the first set of first input pins 302A, . . . , 302G. A first secondary electrode 210B of the first set of first electrodes 210A, . . . , 210G is connected to a first secondary input pin 302B of the first set of first input pins 302A, . . . , 302G. A first tertiary electrode 210C of the first set of first electrodes 210A, . . . , 210G is connected to a first tertiary input pin 302C of the first set of first input pins 302A, . . . , 302G. A first quaternary electrode 210D of the first set of first electrodes 210A, . . . , 210G is connected to a first quaternary input pin 302D of the first set of first input pins 302A, . . . , 302G. A first quinary electrode 210E of the first set of first electrodes 210A, . . . , 210G is connected to a first quinary input pin 302E of the first set of first input pins 302A, . . . , 302G. A first senary electrode 210F of the first set of first electrodes 210A, . . . , 210G is connected to a first senary input pin 302F of the first set of first input pins 302A, . . . , 302G. A first septenary electrode 210G of the first set of first electrodes 210A, . . . , 210G is connected to a first septenary input pin 302G of the first set of first input pins 302A, . . . , 302G. A second primary electrode 212A of the second set of second electrodes 212A, . . . , 212C is connected to a second primary input pin 303A of the second set of second input pins 303A, . . . , 303C. A second secondary electrode 212B of the second set of second electrodes 212A, . . . , 212C is connected to a second secondary input pin 303B of the second set of second input pins 303A, . . . , 303C. A second tertiary electrode 212C of the second set of second electrodes 212A, . . . , 212C is connected to a second tertiary input pin 303C of the second set of second input pins 303A, . . . , 303C.

The multiplexer 217A also comprises a first output pin 304 connected to a first terminal 110 of the monitor interface 102. The multiplexer 217A comprises a second output pin 306 connected to a second terminal 112 of the monitor interface 102. The multiplexer 217A comprises a first control pin 308 connected to a third terminal 114 of the monitor interface 102. The multiplexer 217A comprises a second control pin 310 connected to a fourth terminal 116 of the monitor interface 102. The multiplexer 217A comprises a third control pin 312 connected to a fifth terminal 118 of monitor interface 102. The multiplexer 217A comprises a fourth control pin 314 connected to a sixth terminal 119 of the monitor interface 102.

The control pins 308, 310, 312, 314 are configured to receive control signals from the monitor device 4 via the respective terminals 114, 116, 118, 119 to which they're connected. Depending on the control signals received, the sensor signals from the different electrodes 210A, . . . , 210G, 212A, . . . , 212C can be output via the first output pin and/or the second output pin 306 to the monitor device 4. With the wound dressing 2B including the multiplexer 217A, it is possible to collect data from ten (or more) different electrodes in various multiplexer configurations via a six-terminal connector of the monitor interface 102.

In a first multiplexer configuration example, the multiplexer 217A receives a control signal to connect the first primary electrode 210A, via the first primary input pin 302A, to the first output pin 304. In the first multiplexer configuration, the multiplexer 217A may additionally receive a control signal to connect the second primary electrode 212A, via the second primary input pin 303A, to the second output pin 306.

In a second multiplexer configuration example, the multiplexer 217A receives a control signal to connect the first secondary electrode 210B, via the first secondary input pin 302B, to the first output pin 304. In the second multiplexer configuration, the multiplexer 217A may additionally receive a control signal to connect the second secondary electrode 212B, via the second secondary input pin 303B, to the second output pin 306.

In a third multiplexer configuration example, the multiplexer 217A receives a control signal to connect the first tertiary electrode 210C, via the first tertiary input pin 302C, to the first output pin 304. In the third multiplexer configuration, the multiplexer 217A may additionally receive a control signal to connect the second tertiary electrode 212C, via the second tertiary input pin 303C, to the second output pin 306.

Figure 17:
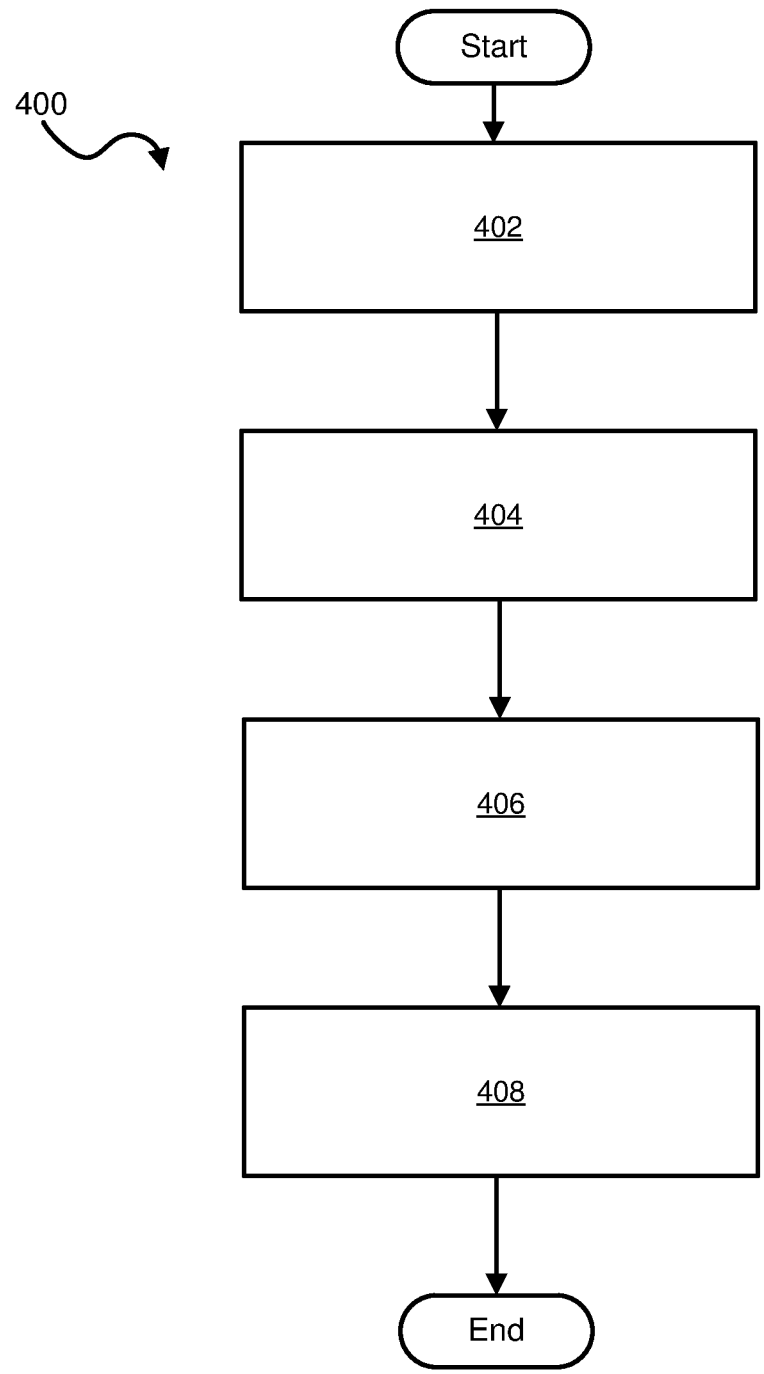
FIG. 17 is a flow diagram of an exemplary method.

FIG. 17 is a flow chart of an exemplary method 400 of manufacturing a wound dressing of a wound dressing system. The method 400 comprises providing a first adhesive layer (e.g., a first adhesive layer 150) including a proximal surface configured for attachment of the wound dressing (e.g. wound dressing 2, 2A, 2B) to a user (block 402). The method 400 further comprises arranging an absorbent core (e.g., the absorbent core 202) on a distal side of the first adhesive layer 150 (block 404).

The method 400 further comprises arranging an electrode assembly (e.g., electrode assembly 204) on a distal side of the absorbent core (block 406). The electrode assembly includes a plurality of electrodes and a multiplexer. The plurality of electrodes includes a first set of first electrodes (e.g., first electrodes 210A, . . . , 210I) and optionally a second set of second electrodes (e.g., second electrodes 212A, . . . , 212C). The method 400 comprises arranging the electrode assembly on the distal side of the absorbent core such that each electrode of the first and second sets of electrodes are connected to a respective input pin of N input pins of the multiplexer. That is, each electrode of the first set of first electrodes is connected to a respective input pin of a first set of first input pins (e.g., first set of first input pins 302A, . . . , 302G) and each electrode of the second set of second electrodes is connected to a respective input pin of a second set of second input pins (e.g., second set of second input pins 303A, . . . , 303C).

In addition, the multiplexer includes a first output pin (e.g., first output pin 304), a second output pin (e.g., second output pin 306), a first control pin (e.g., first control pin 308), a second control pin (e.g., second control pin 310), a third control pin (e.g., third control pin 312), and a fourth control pin (e.g., fourth control pin 314).

The method 400 further comprises arranging a monitor interface (e.g., monitor interface 102) on the distal side of the first adhesive layer (block 408). The monitor interface includes a first terminal (e.g., first terminal 110), a second terminal (e.g., second terminal 112), a third terminal (e.g., third terminal 114), a fourth terminal (e.g., fourth terminal 116), a fifth terminal (e.g., fifth terminal 118), and a sixth terminal (e.g., sixth terminal 119). The monitor interface is arranged on a distal side of the first adhesive layer such that: the first output pin of the multiplexer is connected to the first terminal of the monitor interface, the second output pin of the multiplexer is connected to the second terminal of the monitor interface, the first control pin of the multiplexer is connected to the third terminal of the monitor interface, the second control pin of the multiplexer is connected to the fourth terminal of the monitor interface, the third control pin of the multiplexer is connected to the fifth terminal of the monitor interface, and the fourth control pin of the multiplexer is connected to the sixth terminal of the monitor interface.

Figure 18:
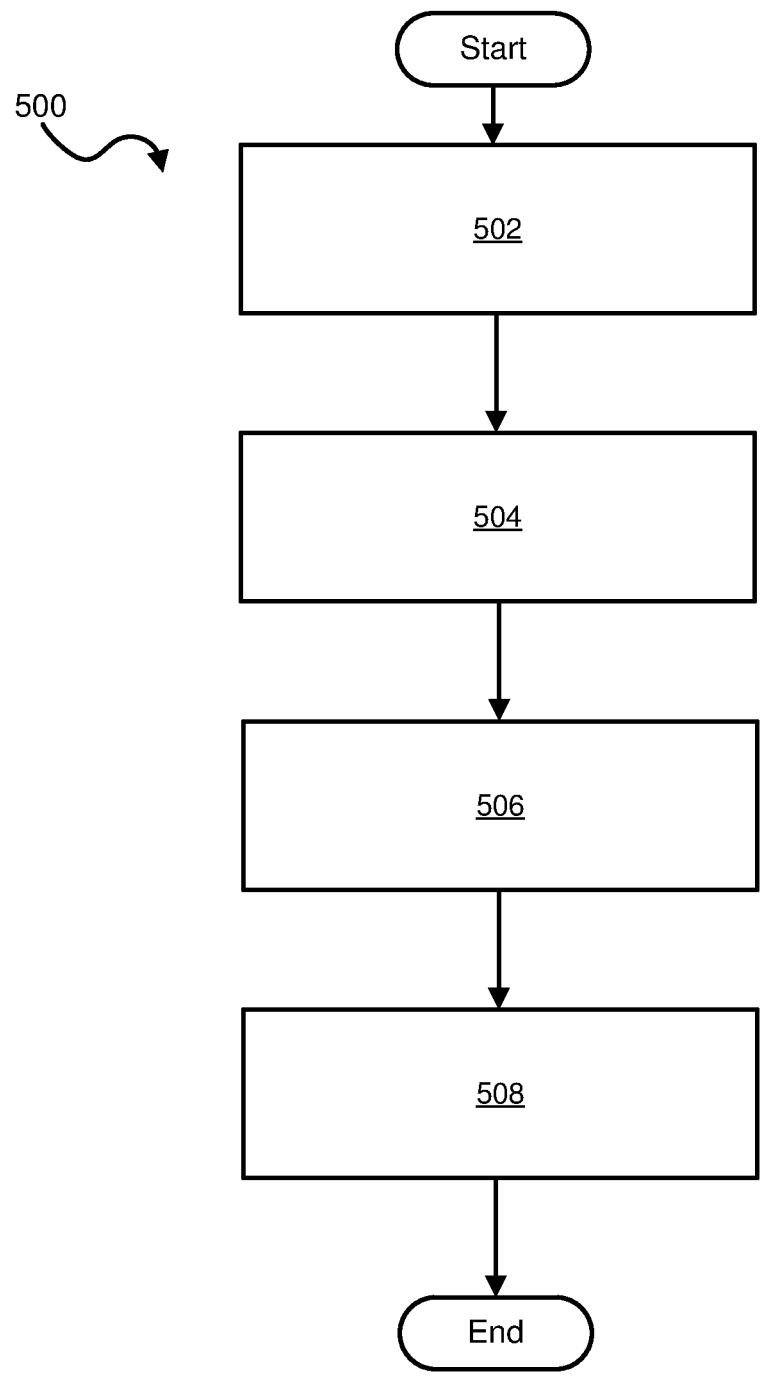
FIG. 18 is a flow diagram of an exemplary method.

FIG. 18 is a flow chart of an exemplary method 500 of monitoring a wound dressing (e.g. wound dressing 2, 2A, 2B) of a wound dressing system. The wound dressing comprises a first adhesive layer (e.g. first adhesive layer 200), a plurality of electrodes on a distal side of the first adhesive layer, a monitor interface, and a multiplexer (e.g. multiplexer 217, 217A). A first output pin of the multiplexer is connected to a first terminal of the monitor interface and a second output pin of the multiplexer is connected to a second terminal of the monitor interface.

The plurality of electrodes includes a first set of first electrodes (e.g. first electrodes 210A, . . . , 210I), and optionally a second set of second electrodes (e.g. second set of second electrodes 212A, . . . , 212C). Each electrode of the first set of first electrodes is connected to a respective input pin of a first set of first input pins (e.g., first set of first input pins 302A, . . . , 302G) of the multiplexer and each electrode of the second set of second electrodes is connected to a respective input pin of a second set of second input pins (e.g., second set of second input pins 303A, . . . , 303C) of the multiplexer.

The method 500 comprises selecting 502 a first multiplexer configuration of the multiplexer (block 502). The first multiplexer configuration includes a first primary electrode of the first set of first electrodes being connected, via a first primary input pin of the first set of first input pins, to the first terminal (e.g., a terminal 110, . . . , 119) of the monitor interface, via the first output pin.

The method 500 further comprises obtaining a first sensor signal from the first terminal of the monitor interface when the multiplexer is in the first multiplexer configuration (block 504).

The method further comprises selecting a second multiplexer configuration of the multiplexer (block 506). The second multiplexer configuration includes a first secondary electrode of the first set of first electrodes being connected, via a first secondary input pin of the first set of first input pins, to the first terminal of the monitor interface, via the first output pin.

The method further comprises obtaining a second sensor signal from the first terminal of the monitor device when the multiplexer is in the second multiplexer configuration (block 508).

Figure 19:
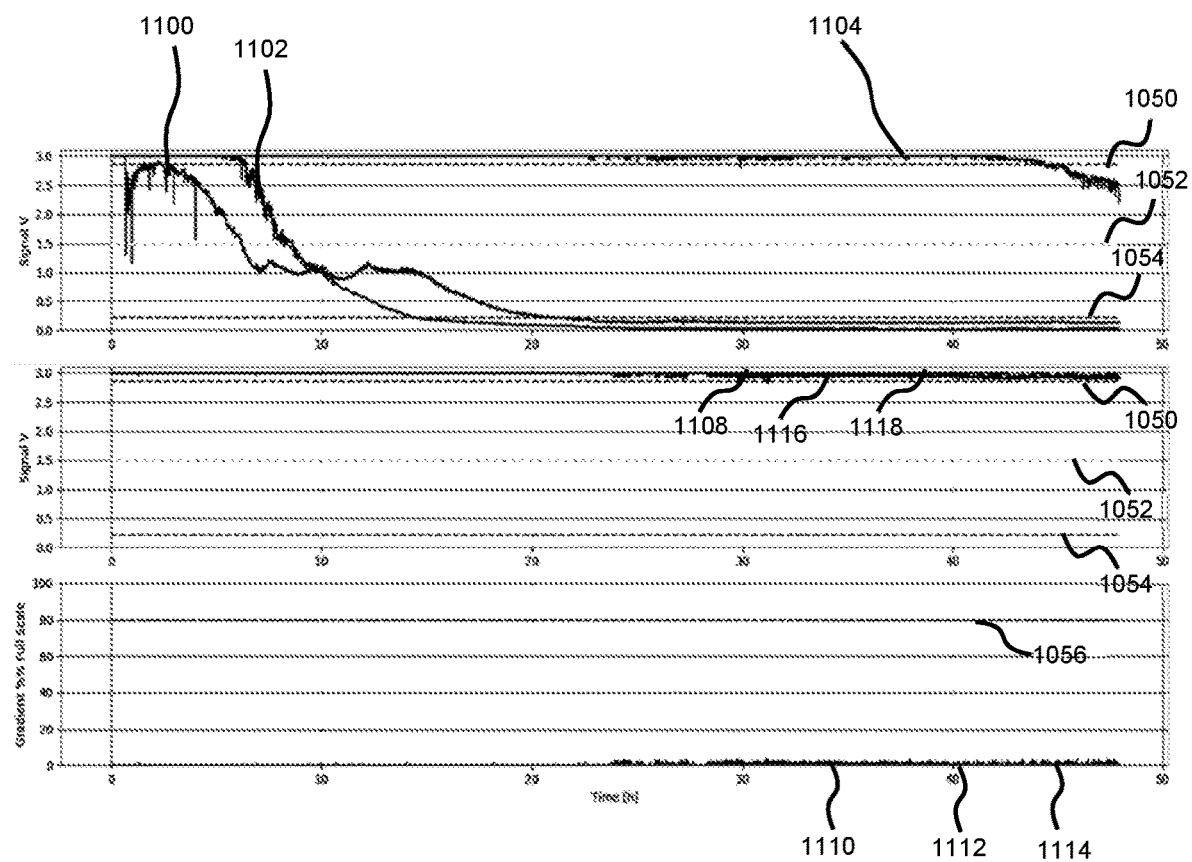
FIG. 19 is an exemplary graphical representation of parameter data as a function of time.

FIG. 19 shows an exemplary graphical representation of parameter data as a function of time. In this example, the parameter data in the y-axis is in Volts and time is in the x-axis. Curve 1100 shows, as a function of time, a first parameter data indicative of voltage measured by the first electrode pair of the wound dressing. Curve 1102 shows, as a function of time, a second parameter data indicative of voltage measured by the second electrode pair of the wound dressing. Curve 1104 shows, as a function of time, a third parameter data indicative of voltage measured by the third electrode pair of the wound dressing. Curves 1108, 1116, 1118 show, as a function of time, a fourth parameter data indicative of voltage measured by the fourth electrode pair of the wound dressing. Curves 1110, 1112, 1114 show, as a function of time, a gradient of fourth parameter data indicative of voltage gradient measured by the fourth electrode pair of the wound dressing. FIG. 19 shows the upper voltage threshold value represented as curve 1050, the medium voltage threshold value represented as curve 1052, the lower voltage threshold value represented as curve 1054, and curve 1056 is a gradient limit.

Curves 1108, 1116, 1118 as well as curves 1110, 1112, 1114 show that no moisture is detected at the proximal side of the first adhesive layer by the fourth electrode pair.

At a time less than 5 $h$, curve 1100 shows that moisture is detected by the first electrode pair as the first parameter data crosses the upper voltage threshold value while curve 1102 shows that moisture is not detected by the second electrode pair as the second parameter data has not crossed the upper voltage threshold value. At this stage, it is determined that the wound dressing is in a first operating state.

At time between 5 *h* and 10 *h*, curve 1101 shows that moisture is detected by the second electrode pair as the second parameter data crosses the upper voltage threshold value. At this stage, it is determined that the wound dressing is in a second operating state.

At time around 45 *h*, curve 1104 shows that moisture is detected by the third electrode pair as the third parameter data crosses the upper voltage threshold value. At this stage, it is determined that the wound dressing is in a third operating state.

Figure 20:
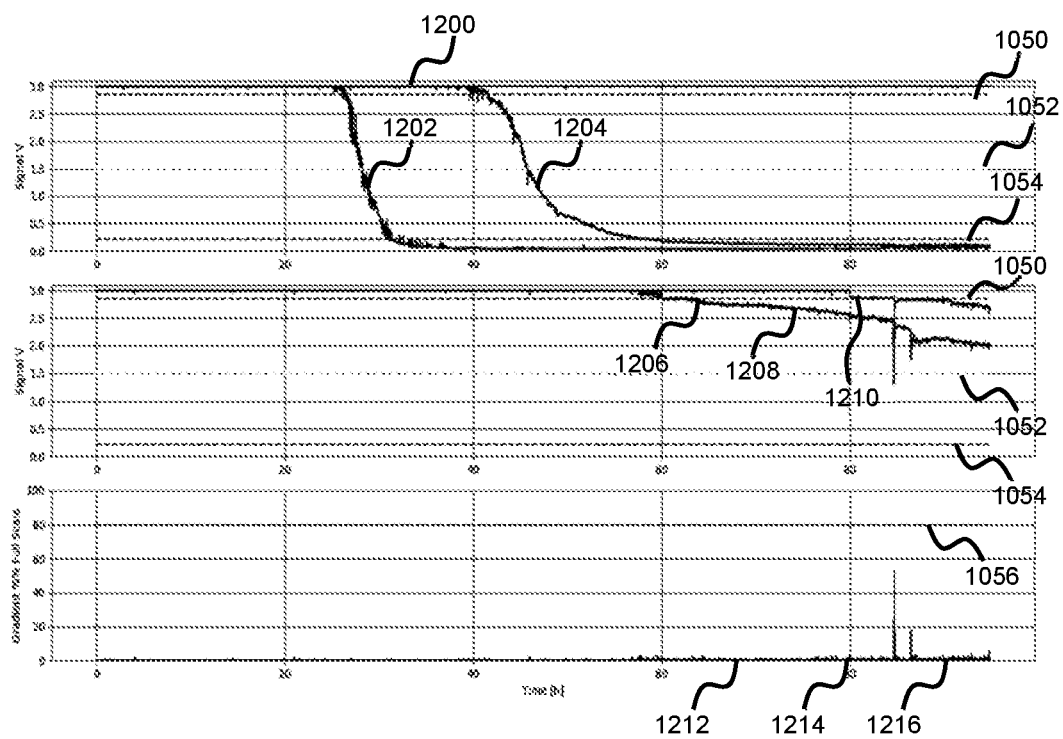
FIG. 20 is an exemplary graphical representation of parameter data as a function of time.

FIG. 20 shows an exemplary graphical representation of parameter data as a function of time. In this example, the parameter data in the y-axis is in Volts and time is in the x-axis. Curve 1202 shows, as a function of time, a first parameter data indicative of voltage measured by the first electrode pair of the wound dressing. Curve 1204 shows, as a function of time, a second parameter data indicative of voltage measured by the second electrode pair of the wound dressing. Curve 1200 shows, as a function of time, a third parameter data indicative of voltage measured by the third electrode pair of the wound dressing. Curves 1206, 1208, 1210 show, as a function of time, a fourth parameter data indicative of voltage measured by the fourth electrode pair of the wound dressing. Curves 1212, 1214, 1216 show, as a function of time, a gradient of fourth parameter data indicative of voltage gradient measured by the fourth electrode pair of the wound dressing. FIG. 20 shows the upper voltage threshold value represented as curve 1050, the medium voltage threshold value represented as curve 1052, the lower voltage threshold value represented as curve 1054, and curve 1056 represents a gradient limit.

Curves 1206, 1208, 1210 as well as curves 1212, 1214, 1216 show that moisture is detected at the proximal side of the first adhesive layer by the fourth electrode pair at a time starting at 60 *h* until 90 *h*. As the three parts of the fourth electrode pair are trigger as shown by the decreases shown by 1206, 1208, 1210 and as the curves 1212, 1214, 1216 show a gradient below 80%, this is indicative of the presence of moisture (e.g., sweat, exudate, etc.) at the proximal side of the first adhesive layer.

At a time of 30 min, curve 1202 shows that moisture is detected by the first electrode pair as the first parameter data crosses the upper voltage threshold value while curve 1204 shows that moisture is not detected by the second electrode pair as the second parameter data has not crossed the upper voltage threshold value. At this stage, it is determined that the wound dressing is in a first operating state.

At time around 40 *h*, curve 1204 shows that moisture is detected by the second electrode pair as the second parameter data crosses the upper voltage threshold value. At this stage, it is determined that the wound dressing is in a second operating state.

Figure 21:
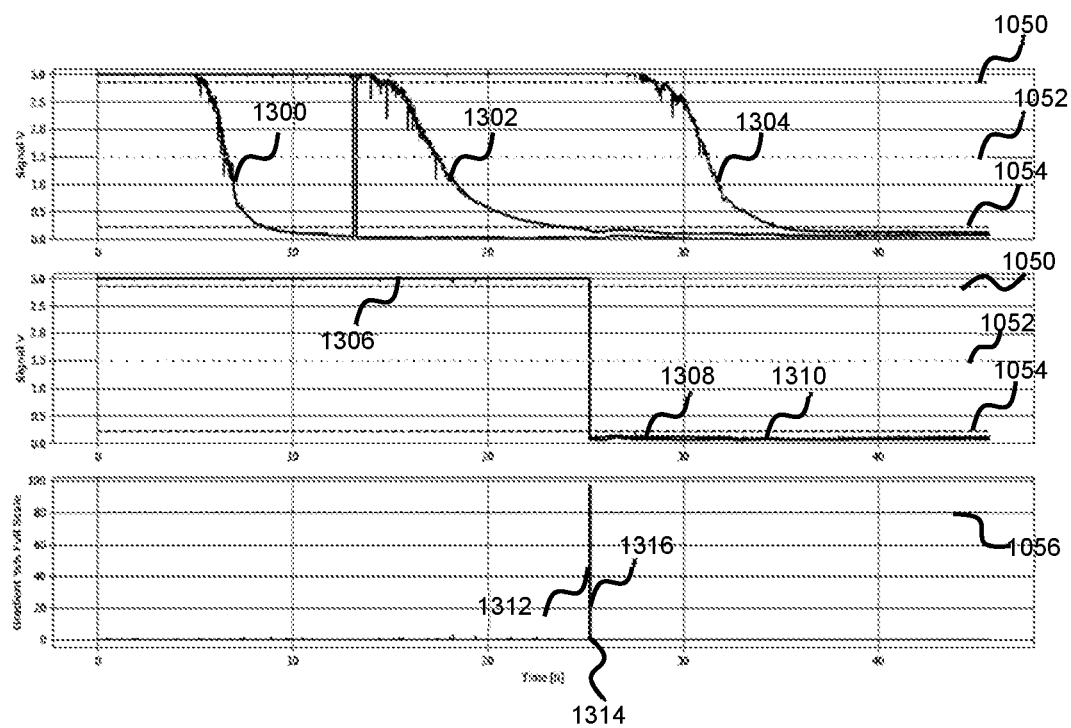
FIG. 21 is an exemplary graphical representation of parameter data as a function of time.

FIG. 21 shows an exemplary graphical representation of parameter data as a function of time. In this example, the parameter data in the y-axis is in Volts and time is in the x-axis. Curve 1300 shows, as a function of time, a first parameter data indicative of voltage measured by the first electrode pair of the wound dressing. Curve 1302 shows, as a function of time, a second parameter data indicative of voltage measured by the second electrode pair of the wound dressing. Curve 1304 shows, as a function of time, a third parameter data indicative of voltage measured by the third electrode pair of the wound dressing. Curves 1306, 1308, 1310 show, as a function of time, a fourth parameter data indicative of voltage measured by the fourth electrode pair of the wound dressing. Curves 1312, 1314, 1316 show, as a function of time, a gradient of fourth parameter data indicative of voltage gradient measured by the fourth electrode pair of the wound dressing. FIG. 21 shows the upper voltage threshold value represented as curve 1050, the medium voltage threshold value represented as curve 1052, the lower voltage threshold value represented as curve 1054, and curve 1056 is a gradient limit.

Curves 1306, 1308, 1310 as well as curves 1312, 1314, 1316 show that moisture is detected at the proximal side of the first adhesive layer by the fourth electrode pair at a time starting at around 25 *h*. As the three parts of the fourth electrode pair are trigger as shown by the decreases shown by 1306, 1308, 1310 and as the curves 1312, 1314, 1316 show a gradient above 80%, this is indicative of the presence of moisture at the proximal side of the first adhesive layer. This may indicate a low degree of remaining absorbent capacity of the wound dressing/absorbent core layer.

At a time of 5 *h*, curve 1300 shows that moisture is detected by the first electrode pair as the first parameter data crosses the upper voltage threshold value while curve 1302 shows that moisture is not detected by the second electrode pair as the second parameter data has not crossed the upper voltage threshold value. At this stage, it is determined that the wound dressing is in a first operating state.

At time around 15 *h*, curve 1302 shows that moisture is detected by the second electrode pair as the second parameter data crosses the upper voltage threshold value. At this stage, it is determined that the wound dressing is in a second operating state.

At time around 30 *h*, curve 1304 shows that moisture is detected by the third electrode pair as the third parameter data crosses the upper voltage threshold value. At this stage, it is determined that the wound dressing is in a third operating state.

As of note, the graphical representations of parameter data as a function of time represented in FIGS. 19-21 are presented for illustration purposes and the times may vary depending on the size and severity of the wound to which the wound dressing is applied.

The use of the terms "first", "second", "third" and "fourth", "primary", "secondary", "tertiary" etc. does not imply any particular order but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 1 wound dressing system
2, 2A, 2B wound dressing 4 monitor device
6 accessory device
8 server device
10 network
20 docking station
22 first connector
24 user interface
100 monitor device housing
101 processor
102 first interface (wound dressing interface)
104 second interface (accessory interface)
106 memory
110 first terminal
112 second terminal
114 third terminal
116 fourth terminal
118 fifth terminal
119 sixth terminal
120 coupling part
121 power unit
122 antenna
124 wireless transceiver
126 loudspeaker
128 haptic feedback element
140 sensor unit
150 first adhesive layer
150A proximal surface of the first adhesive layer
152 perforations of first adhesive layer
154 absorbing region
200 wound dressing
202 absorbent core layer
204, 204A, 204B electrode assembly
206 top layer
208 first support layer
208A proximal surface of first support layer
208B distal surface of first support layer
210 first set of first electrodes
210A, 210B, 210C, 210D, 210E, 210F, 210G, 210G, 210I first electrode
212 second set of second electrodes
212A, 212B, 212C second electrode
214 sensor point
215 connection parts of plurality of electrodes
216 first masking layer
217, 217A multiplexer
218 first sensing part of first electrode
220 second sensing part of second electrode
222 sensor point opening of first masking layer
224 second support layer
224A proximal surface of second support layer
224B distal surface of second support layer
226 spacing layer
250 sensor point opening of first support layer
252 connection point of first electrode
254 sensor point opening of second support layer
256 connection point of second electrode
270, 270A second masking layer
302 first set of first input pins
302A, 302B, 302C, 302D, 302E, 302F, 302G first input pins
303 second set of second input pins
303A, 303B, 303C second input pins
304 first output pin
306 second output pin
308 first control pin
310 second control pin
312 third control pin
314 fourth control pin
400 method of manufacturing a wound dressing
402 provide a first adhesive layer
404 arrange an absorbent core on a distal side of the first adhesive layer
406 arrange an electrode assembly on the distal side of the first adhesive layer
408 arrange a monitor interface on the distal side of the first adhesive layer
500 method of monitoring a wound dressing
502 select a first multiplexer configuration of the multiplexer
504 obtain a first sensor signal from the first terminal of the monitor device
506 select a second multiplexer configuration of the multiplexer
508 obtain a second sensor signal from the first terminal of the monitor device
1000 method of monitoring a wound dressing comprising an absorbent core layer
1002 collecting wound data
1003 obtaining parameter data
1004 obtaining first parameter data
1006 obtaining second parameter data
1008 obtaining third parameter data
1010 obtaining fourth parameter data
1011 determining operating state of wound dressing
1012 in accordance with a determination that the operating state is a first operating state
1014 transmitting a first monitor signal
1016 in accordance with a determination that the operating state is a second operating state
1018 transmitting a second monitor signal
1050 curve representing the upper voltage threshold value
1052 curve representing the medium voltage threshold value
1054 curve representing the lower voltage threshold value
1056 curve representing a gradient limit
1100 curve showing, as a function of time, a first parameter data indicative of voltage measured by the first electrode pair of the wound dressing
1102 curve showing, as a function of time, a second parameter data indicative of voltage measured by the second electrode pair of the wound dressing
1104 curve showing, as a function of time, a third parameter data indicative of voltage measured by the third electrode pair of the wound dressing
1108 curve showing, as a function of time, a fourth parameter data indicative of voltage measured by the fourth electrode pair of the wound dressing
1110 curve showing, as a function of time, a gradient of fourth parameter data indicative of voltage gradient measured by the fourth electrode pair of the wound dressing
1112 curve showing, as a function of time, a gradient of fourth parameter data indicative of voltage gradient measured by the fourth electrode pair of the wound dressing
1114 curve showing, as a function of time, a gradient of fourth parameter data indicative of voltage gradient measured by the fourth electrode pair of the wound dressing
1116 curve showing, as a function of time, a fourth parameter data indicative of voltage measured by the fourth electrode pair of the wound dressing 1118 curve showing, as a function of time, a fourth parameter data indicative of voltage measured by the fourth electrode pair of the wound dressing 1200 curve showing, as a function of time, a third parameter data indicative of voltage measured by the third electrode pair of the wound dressing 1202 curve showing, as a function of time, a first parameter data indicative of voltage measured by the first electrode pair of the wound dressing 1204 curve showing, as a function of time, a second parameter data indicative of voltage measured by the second electrode pair of the wound dressing 1206 curve showing, as a function of time, a fourth parameter data indicative of voltage measured by the fourth electrode pair of the wound dressing 1208 curve showing, as a function of time, a fourth parameter data indicative of voltage measured by the fourth electrode pair of the wound dressing 1210 curve showing, as a function of time, a fourth parameter data indicative of voltage measured by the fourth electrode pair of the wound dressing 1212 curve showing, as a function of time, a gradient of fourth parameter data indicative of voltage gradient measured by the fourth electrode pair of the wound dressing 1214 curve showing, as a function of time, a gradient of fourth parameter data indicative of voltage gradient measured by the fourth electrode pair of the wound dressing 1216 curve showing, as a function of time, a gradient of fourth parameter data indicative of voltage gradient measured by the fourth electrode pair of the wound dressing 1300 curve showing, as a function of time, a first parameter data indicative of voltage measured by the first electrode pair of the wound dressing 1302 curve showing, as a function of time, a second parameter data indicative of voltage measured by the second electrode pair of the wound dressing 1304 curve showing, as a function of time, a third parameter data indicative of voltage measured by the third electrode pair of the wound dressing 1306 curve showing, as a function of time, a fourth parameter data indicative of voltage measured by the fourth electrode pair of the wound dressing 1308 curve showing, as a function of time, a fourth parameter data indicative of voltage measured by the fourth electrode pair of the wound dressing 1310 curve showing, as a function of time, a fourth parameter data indicative of voltage measured by the fourth electrode pair of the wound dressing 1312 curve showing, as a function of time, a gradient of fourth parameter data indicative of voltage gradient measured by the fourth electrode pair of the wound dressing 1314 curve showing, as a function of time, a gradient of fourth parameter data indicative of voltage gradient measured by the fourth electrode pair of the wound dressing 1316 curve showing, as a function of time, a gradient of fourth parameter data indicative of voltage gradient measured by the fourth electrode pair of the wound dressing

The invention claimed is:

1. A wound dressing comprising:
    a first adhesive layer comprising a proximal surface configured for attachment of the wound dressing to a skin surface of a user;
    an electrode assembly comprising a plurality of electrodes including a first set of first electrodes;
    a monitor interface for forming a mechanical and electrical connection with a monitor device, the monitor interface comprising a coupling part and a plurality of terminals including a first terminal; and
    a multiplexer comprising a number of N input pins and a number of M output pins, wherein the N input pins include a first set of first input pins for connection to first electrodes of the first set of first electrodes, the first set of first pins including a first primary input pin and a first secondary input pin, and the M output pins include a first output pin,
    wherein the first primary input pin is connected to a first primary electrode of the first set of first electrodes and the first secondary input pin is connected to a first secondary electrode of the first set of first electrodes, and the first output pin is connected to the first terminal of the monitor interface, and
    wherein the multiplexer is configured to select a multiplexer configuration from a set of multiplexer configurations based on a control signal received via a control pin of the monitor interface, the set of multiplexer configurations comprising:
        a first multiplexer configuration where the first primary input pin is connected to the first output pin; and
        a second multiplexer configuration where the first secondary input pin is connected to the first output pin.

2. The wound dressing of claim 1, wherein the monitor interface includes at least seven terminals that each correspond to an output pin of the M output pins.

3. The wound dressing of claim 2, wherein the plurality of electrodes comprises at least nine electrodes that each correspond to an input pin of the N input pins.

4. The wound dressing according to claim 1, wherein the monitor interface comprises a second terminal, and wherein the M output pins include a second output pin connected to the second terminal.

5. The wound dressing according to claim 1,
    wherein the plurality of electrodes comprise a second set of second electrodes including a second primary electrode and a second secondary electrode, wherein the N input pins comprise a second set of second input pins for connection to second electrodes of the second set of second electrodes, wherein a second primary input pin of the second set of second input pins is connected to the second primary electrode and a second secondary input pin of the second set of second input pins is connected to the second secondary electrode; and
    the multiplexer is configured to connect the second primary input pin to the second output pin in the first multiplexer configuration and to connect the second secondary input pin to the second output pin in the second multiplexer configuration.

6. The wound dressing according to claim 1,
    wherein the first set of first electrodes comprises a first tertiary electrode, wherein a first tertiary input pin of the first set of first input pins is connected to the first tertiary input pin; and
    wherein the multiplexer is configured to connect the first tertiary input pin to the first output pin in a third multiplexer configuration.

7. The wound dressing according to claim 1,
wherein the second set of second electrodes comprise a second tertiary electrode, wherein a second tertiary input pin of the second set of second input pins is connected to the second tertiary electrode; and
wherein the multiplexer is configured to connect the second tertiary input pin to the second output pin in a third multiplexer configuration.

8. The wound dressing according to claim 1, wherein the control pin is a first control pin, wherein the multiplexer comprises a second control pin, and wherein the multiplexer is configured to select a multiplexer scheme based on a second control signal received by the second control pin.

9. The wound dressing according to claim 1, wherein the multiplexer is embedded in the electrode assembly.

10. The wound dressing according to claim 1, wherein the multiplexer is embedded in the coupling part of the monitor interface.

11. The wound dressing of claim 1, wherein
the plurality of electrodes further comprises a second set of electrodes; and
the number of N input pins further comprises a second set of input pins that each correspond to an electrode of the second set of electrodes.

12. A wound dressing comprising:
an adhesive layer comprising a proximal surface configured for attachment of the wound dressing to a skin surface of a user;
an electrode assembly comprising a plurality of electrodes including a first set of first electrodes;
a monitor interface for forming a connection with a monitor device; and
a multiplexer comprising a number of N input pins and a number of M output pins, wherein the N input pins include a first set of first input pins for connection to electrodes of the first set of first electrodes, the first set of first pins including a first primary input pin and a first secondary input pin, and the M output pins include a first output pin,
wherein the first primary input pin is connected to a first primary electrode of the first set of first electrodes and the first secondary input pin is connected to a first secondary electrode of the first set of first electrodes, and the first output pin is connected to a terminal of the monitor interface, and
wherein the multiplexer is configured to select a multiplexer configuration from a set of multiplexer configurations based on a control signal received via a control pin of the monitor interface, the set of multiplexer configurations comprising:
a first multiplexer configuration where the first primary input pin is connected to the first output pin; and
a second multiplexer configuration where the first secondary input pin is connected to the first output pin.

13. The wound dressing according to claim 12, wherein the terminal is a first terminal and the monitor interface comprises a second terminal, and wherein the M output pins include a second output pin connected to the second terminal.

14. The wound dressing according to claim 12,
wherein the plurality of electrodes comprise a second set of second electrodes including a second primary electrode and a second secondary electrode, wherein the N input pins comprise a second set of second input pins for connection to second electrodes of the second set of second electrodes, wherein a second primary input pin of the second set of second input pins is connected to the second primary electrode and a second secondary input pin of the second set of second input pins is connected to the second secondary electrode; and
the multiplexer is configured to connect the second primary input pin to the second output pin in the first multiplexer configuration and to connect the second secondary input pin to the second output pin in the second multiplexer configuration.

15. The wound dressing according to claim 12,
wherein the first set of first electrodes comprises a first tertiary electrode, wherein a first tertiary input pin of the first set of first input pins is connected to the first tertiary input pin; and
wherein the multiplexer is configured to connect the first tertiary input pin to the first output pin in a third multiplexer configuration.

16. The wound dressing according to claim 12,
wherein the second set of second electrodes comprise a second tertiary electrode, wherein a second tertiary input pin of the second set of second input pins is connected to the second tertiary electrode; and
wherein the multiplexer is configured to connect the second tertiary input pin to the second output pin in a third multiplexer configuration.

17. The wound dressing according to claim 12, wherein the control pin is a first control pin, wherein the multiplexer comprises a second control pin, and wherein the multiplexer is configured to select a multiplexer scheme based on a second control signal received by the second control pin.

18. The wound dressing according to claim 12, wherein the multiplexer is embedded in the electrode assembly.

19. The wound dressing according to claim 12, wherein the multiplexer is embedded in a coupling part of the monitor interface.

20. The wound dressing of claim 12, wherein
the plurality of electrodes further comprises a second set of electrodes; and
the number of N input pins further comprises a second set of input pins that each correspond to an electrode of the second set of electrodes.

* * * * *